(12) United States Patent
Chaux et al.

(10) Patent No.: US 6,369,211 B1
(45) Date of Patent: Apr. 9, 2002

(54) MAGE-3 PEPTIDES PRESENTED BY HLA CLASS II MOLECULES

(75) Inventors: Pascal Chaux; Vincent Stroobant; Thierry Boon-Falleur; Pierre van der Bruggen, all of Brussels (BE)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 09/348,933

(22) Filed: Jul. 7, 1999

Related U.S. Application Data

(62) Division of application No. 08/928,615, filed on Sep. 12, 1997, now Pat. No. 5,965,535.

(51) Int. Cl.⁷ .................. C07H 21/02; C07H 21/04; C12N 15/00; C12N 5/10; C12N 5/06
(52) U.S. Cl. .................. 536/23.5; 536/23.1; 536/23.4; 435/320.1; 435/350; 435/363; 435/325
(58) Field of Search ................ 536/23.5, 23.4, 536/23.1; 435/320.1, 350, 363, 325

(56) References Cited

U.S. PATENT DOCUMENTS

| | | |
|---|---|---|
| 5,342,774 A | 8/1994 | Boon et al. |
| 5,405,940 A | 4/1995 | Boon et al. |
| 5,585,461 A | 12/1996 | Townsend et al. |
| 5,591,430 A | 1/1997 | Townsend et al. |

FOREIGN PATENT DOCUMENTS

| | | |
|---|---|---|
| WO | PCT/US92/04354 | 11/1992 |
| WO | PCT/US93/08157 | 3/1994 |
| WO | PCT/US94/02877 | 10/1994 |
| WO | PCT/US95/01000 | 7/1995 |
| WO | PCT/US95/03657 | 9/1995 |
| WO | PCT/US96/15346 | 9/1996 |
| WO | PCT/US96/16319 | 4/1997 |

OTHER PUBLICATIONS

De Plaen et al., *Immunogenetics* 40:360–369 (1994).
Traversari et al., *Immunogenetics* 35:145 (1992).
van der Bruggen et al., *Science* 254–1643 (1991).
Topalian, *Curr. Opin. Immunol.* 6:741–745, (1994).
Yee et al., *J. Immunol.*, 157:4079–4086 (1996).
Topalian et al., *J. Exp. Med* 183:1965–1971 (1996).
Sanderson et al., *Proc. Nat'l. Acad. Sci. USA* 92:7217–7221 (1995).
Wu et al., *Proc. Nat'l Acad Sci USA* 92:11671–11675 (1995.
Gaugler et al., *J. Exp. Med.* 179:921–930 (1994).
van der Bruggen et al., *Eur. J. Immunol.*, 24:3038–3043 (1994).
Herman et al., *Immunogenetics*, 43:377–383 (1996).
Spatola et al., "Peptide backbone modifications: a structure-activity analysis of peptides containing amide bond surrogates," in Chemistry and Biochemistry of Amino Acids, Peptides, and Proteins, Chapter 5, pp. 267–357, 1983.

*Primary Examiner*—Geetha P. Bansal
(74) *Attorney, Agent, or Firm*—Wolf, Greenfield & Sacks, P.C.

(57) ABSTRACT

The invention describes the HLA class II binding peptides encoded by the MAGE-3 tumor associated gene, as well as nucleic acids encoding such peptides and antibodies relating thereto. The peptides stimulate the activity and proliferation of $CD4^+$ T lymphocytes. Methods and products also are provided for diagnosing and treating conditions characterized by expression of the MAGE-3 gene.

17 Claims, 7 Drawing Sheets

US 6,369,211 B1

MAGE-3 PEPTIDES PRESENTED BY HLA CLASS II MOLECULES

Related Applications

This application is a divisional of application Ser. No. 08/928,615, filed Sep. 12, 1997, entitled MAGE-3 PEPTIDES PRESENTED BY HLA CLASS II MOLECULES, and now issued as U.S. Pat. No. 5,965,535.

FIELD OF THE INVENTION

This invention relates to fragments of the tumor associated gene product MAGE-3 which bind to and are presented to T lymphocytes by HLA class II molecules. The peptides, nucleic acid molecules which code for such peptides, as well as related antibodies and $CD4^+$ T lymphocytes, are useful, inter alia, in diagnostic and therapeutic contexts.

BACKGROUND OF THE INVENTION

The process by which the mammalian immune system recognizes and reacts to foreign or alien materials is complex. An important facet of the system is the T cell response, which in part comprises mature T lymphocytes which are positive for either CD4 or CD8 cell surface proteins. T cells can recognize and interact with other cells via cell surface complexes on the other cells of peptides and molecules referred to as human leukocyte antigens ("HLAs") or major histocompatibility complexes ("MHCs"). The peptides are derived from larger molecules which are processed by the cells which also present the HLA/MHC molecule. See Male et al., *Advanced Immunology* (J.P. Lipincott Company, 1987), especially chapters 6–10. The interaction of T cells and complexes of HLA/peptide is restricted, requiring a specific T cell for a specific complex of an HLA molecule and a peptide. If a specific T cell is not present, there is no T cell response even if its partner complex is present. Similarly, there is no response if the specific complex is absent, but the T cell is present. The mechanisms described above are involved in the immune system's response to foreign materials, in autoimmune pathologies, and in responses to cellular abnormalities.

The T cell response to foreign antigens includes both cytolytic T lymphocytes and helper T lymphocytes. $CD8^+$ cytotoxic or cytolytic T cells (CTLs) are T cells which, when activated, lyse cells that present the appropriate antigen presented by HLA class I molecules. $CD4^+$ T helper cells are T cells which secrete cytokines to stimulate macrophages and antigen-producing B cells which present the appropriate antigen by HLA class II molecules on their surface.

The mechanism by which T cells recognize alien materials also has been implicated in cancer. A number of cytolytic T lymphocyte (CTL) clones directed against autologous melanoma have been described. In some instances, the antigens recognized by these clones have been characterized. In De Plaen et al., *Immunogenetics* 40:360–369 (1994), the "MAGE" family, a family of genes encoding tumor specific antigens, is described. (See also PCT application PCT/US92/04354, published on Nov. 26, 1992.) The expression products of these genes are processed into peptides which, in turn, are expressed on cell surfaces. This can lead to lysis of the tumor cells by specific CTLs. The genes are said to code for "tumor rejection antigen precursors" or "TRAP" molecules, and the peptides derived therefrom are referred to as "tumor rejection antigens" or "TRAs". See Traversari et al., *Immunogenetics* 35: 145 (1992); van der Bruggen et al., *Science* 254: 1643 (1991), for further information on this family of genes. Also, see U.S. Pat. No. 5,342,774.

In U.S. Pat. No. 5,405,940, MAGE nonapeptides are taught which are presented by the HLA-A1 molecule. Given the known specificity of particular peptides for particular HLA molecules, one should expect a particular peptide to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. Pat. No. 5,591,430, additional isolated MAGE-3 peptides are taught which are presented by the HLA-A2 molecule. Therefore, a given TRAP can yield a plurality of TRAs.

The foregoing references describe isolation and/or characterization of tumor rejection antigens which are presented by HLA class I molecules. These TRAs can induce activation and proliferation of $CD8^+$ cytotoxic T lymphocytes (CTLs) which recognize tumor cells that express the tumor associated genes (e.g. MAGE genes) which encode the TRAs.

The importance of $CD4^+$ T lymphocytes (helper T cells) in antitumor immunity has been demonstrated in animal models in which these cells not only serve cooperative and effector functions, but are also critical in maintaining immune memory (reviewed by Topalian, *Curr. Opin. Immunol.* 6:741–745, 1994). Moreover, several studies support the contention that poor tumor-specific immunity is due to inadequate activation of T helper cells.

It has recently been demonstrated that the tyrosinase gene encodes peptides which are presented by HLA class II molecules to stimulate $CD4^+$ T lymphocytes (Topalian et al., 1994; Yee et al., *J. Immunol.* 157:4079–4086, 1996; Topalian et al., *J. Exp. Med.* 183:1965–1971, 1996).

It now has been discovered that the MAGE-3 gene encodes additional tumor rejection antigens which are HLA class II binding peptides. These peptides, when presented by an antigen presenting cell having an HLA class II molecule, effectively induce the activation and proliferation of $CD4^+$ T lymphocytes.

The invention is elaborated upon in the disclosure which follows.

SUMMARY OF THE INVENTION

The invention provides isolated MAGE-3 peptides, and functional variants thereof, which bind HLA class II molecules. The invention also provides isolated nucleic acid molecules encoding such peptides, expression vectors containing those nucleic acid molecules, host cells transfected with those nucleic acid molecules, and antibodies to those peptides and complexes of the peptides and HLA class II antigen presenting molecules. T lymphocytes which recognize complexes of the peptides and HLA class II antigen presenting molecules are also provided. Kits containing the foregoing molecules additionally are provided. The foregoing can be used in the diagnosis or treatment of conditions characterized by the expression of MAGE-3.

According to one aspect of the invention, an isolated HLA class II-binding peptide is provided. The isolated peptide comprises the amino acid sequence of SEQ ID NO:11, or a functional variant thereof. In certain embodiments, the isolated HLA class II-binding peptide comprises the amino acid sequence of SEQ ID NO:9. In preferred embodiments, the isolated HLA class II-binding peptide consists essentially of an amino acid sequence selected from the group consisting of SEQ ID NO:3, SEQ ID NO:4, SEQ ID NO:9, SEQ ID NO:10 and SEQ ID NO:11. In particularly preferred embodiments, the isolated peptide consists of an amino acid sequence selected from the group consisting of SEQ ID NO:3, SEQ ID NO:4, SEQ ID NO:9, SEQ ID NO:10 and SEQ ID NO:11. More preferably, the isolated peptide consists of an amino acid sequence selected from the group consisting of SEQ ID NO:3 and SEQ ID NO:4. In other embodiments of the invention, the isolated HLA class II-binding peptide is non-hydrolyzable. Preferred non-hydrolyzable peptides are selected from the group consisting of peptides comprising D-amino acids, peptides comprising a -psi[$CH_2NH$]-reduced amide peptide bond, peptides comprising a -psi[$COCH_2$]-ketomethylene peptide bond, peptides comprising a-psi[CH(CN)NH]-(cyanomethylene) amino peptide bond, peptides comprising a-psi[$CH_2CH(OH)$]-hydroxyethylene peptide bond, peptides comprising a -psi[$CH_2O$]-peptide bond, and peptides comprising a -psi[$CH_2S$]-thiomethylene peptide bond.

According to another aspect of the invention, a composition comprising an isolated MAGE-3 HLA class I-binding peptide and an isolated MAGE-3 HLA class II-binding peptide is provided. In certain embodiments the isolated MAGE-3 HLA class II-binding peptide in the composition comprises the amino acid sequence of SEQ ID NO:11, or a functional variant thereof. Preferably, the isolated MAGE-3 HLA class II-binding peptide in the composition consists of an amino acid sequence selected from the group consisting of SEQ ID NO:3, SEQ ID NO:4, SEQ ID NO:9, SEQ ID NO:10 and SEQ ID NO:11. More preferably, the isolated MAGE-3 HLA class II-binding peptide consists of an amino acid sequence selected from the group consisting of SEQ ID NO:3 and SEQ ID NO:4.

According to another aspect of the invention, an isolated nucleic acid encoding any of the foregoing HLA class II-binding peptide peptides is provided. Preferably the nucleic acid comprises SEQ ID NO:13.

According to still another aspect of the invention, expression vectors are provided. The expression vectors comprise any of the foregoing isolated nucleic acids operably linked to a promoter. In preferred embodiments, the nucleic acid comprises SEQ ID NO:13. In other embodiments, the expression vector further comprise a nucleic acid which encodes an HLA-DRB1/13 molecule.

According to yet another aspect of the invention, host cells transfected or transformed with any of the foregoing expression vectors are provided. Host cells which express an HLA-DRB1/13 molecule, and which are transfected or transformed with any of the foregoing expression vectors are also provided.

According to another aspect of the invention, methods for enriching selectively a population of T lymphocytes with CD4$^+$ T lymphocytes specific for a MAGE-3 HLA class II-binding peptide are provided. The methods include contacting an isolated population of T lymphocytes with an agent presenting a complex of the MAGE-3 HLA class II-binding peptide and an HLA class II molecule in an amount sufficient to selectively enrich the isolated population of T lymphocytes with the CD4$^+$ T lymphocytes. In certain embodiments, the agent is an antigen presenting cell contacted with a MAGE-3 protein or an HLA class II binding fragment thereof. In preferred embodiments, the HLA class II molecule is an HLA-DRB1/13 molecule and the MAGE-3 HLA class II-binding peptide is selected from the group consisting of a peptide consisting of the amino acid sequence of SEQ ID NO:3, a peptide consisting of the amino acid sequence of SEQ ID NO:4, peptide consisting of the amino acid sequence of SEQ ID NO:9, peptide consisting of the amino acid sequence of SEQ ID NO:10, and a peptide consisting of the amino acid sequence of SEQ ID NO:11. More preferably, the MAGE-3 HLA class II-binding peptide is selected from the group consisting of a peptide consisting of the amino acid sequence of SEQ ID NO:3 and a peptide consisting of the amino acid sequence of SEQ ID NO:4.

According to a further aspect of the invention, methods for diagnosing a disorder characterized by expression of MAGE-3 are provided. The methods include contacting a biological sample isolated from a subject with an agent that is specific for the MAGE-3 HLA class II binding peptide, and determining the interaction between the agent and the MAGE-3 HLA class II binding peptide as a determination of the disorder. In certain embodiments, the peptide comprises the amino acid sequence of SEQ ID NO:11, or a functional variant thereof. In preferred embodiments, the MAGE-3 HLA class II-binding peptide is selected from the group consisting of a peptide consisting of the amino acid sequence of SEQ ID NO:3, a peptide consisting of the amino acid sequence of SEQ ID NO:4, peptide consisting of the amino acid sequence of SEQ ID NO:9, peptide consisting of the amino acid sequence of SEQ ID NO:10, and a peptide consisting of the amino acid sequence of SEQ ID NO:11. More preferably, the MAGE-3 HLA class II-binding peptide is selected from the group consisting of a peptide consisting of the amino acid sequence of SEQ ID NO:3 and a peptide consisting of the amino acid sequence of SEQ ID NO:4.

According to another aspect of the invention, methods for diagnosing a disorder characterized by expression of a MAGE-3 HLA class II-binding peptide which forms a complex with an HLA class II molecule are provided. The methods include contacting a biological sample isolated from a subject with an agent that binds the complex; and determining binding between the complex and the agent as a determination of the disorder. In some embodiments the HLA class II molecule is an HLA-DRB1/13 molecule, such as HLA-DRB1/1301 or HLA-DRB1/1302, and the MAGE-3 HLA class II-binding peptide comprises the amino acid sequence of SEQ ID NO:11, or a functional variant thereof. Preferably the MAGE-3 HLA class II-binding peptide is selected from the group consisting of a peptide consisting of the amino acid sequence of SEQ ID NO:3, a peptide consisting of the amino acid sequence of SEQ ID NO:4, peptide consisting of the amino acid sequence of SEQ ID NO:9, peptide consisting of the amino acid sequence of SEQ ID NO:10, and a peptide consisting of the amino acid sequence of SEQ ID NO:11. More preferably, the MAGE-3 HLA class II-binding peptide is selected from the group consisting of a peptide consisting of the amino acid sequence of SEQ ID NO:3 and a peptide consisting of the amino acid sequence of SEQ ID NO:4.

Methods for treating a subject having a disorder characterized by expression of MAGE-3 are provided in another aspect of the invention. The methods include administering to the subject an amount of a MAGE-3 HLA class II-binding peptide sufficient to ameliorate the disorder. In certain embodiments the MAGE-3 HLA class II-binding peptide comprises the amino acid sequence of SEQ ID NO:11, or a functional variant thereof. Preferably the peptide is selected from the group consisting of a peptide consisting of the amino acid sequence of SEQ ID NO:3, a peptide consisting of the amino acid sequence of SEQ ID NO:4, peptide consisting of the amino acid sequence of SEQ ID NO:9, peptide consisting of the amino acid sequence of SEQ ID NO:10, and a peptide consisting of the amino acid sequence of SEQ ID NO:11. More preferably, the MAGE-3 HLA class II-binding peptide is selected from the group consisting of a peptide consisting of the amino acid sequence of SEQ ID NO:3 and a peptide consisting of the amino acid sequence of SEQ ID NO:4.

According to still another aspect of the invention, methods for treating a subject having a disorder characterized by expression of MAGE-3 are provided. The methods include administering to the subject an amount of a MAGE-3 HLA class I-binding peptide and an amount of a MAGE-3 HLA class II-binding peptide sufficient to ameliorate the disorder. In certain embodiments, the MAGE-3 HLA class II-binding peptide comprises the amino acid sequence of SEQ ID NO:11, or a functional variant thereof. Preferably the peptide is selected from the group consisting of a peptide consisting of the amino acid sequence of SEQ ID NO:3, a peptide consisting of the amino acid sequence of SEQ ID NO:4, peptide consisting of the amino acid sequence of SEQ ID NO:9, peptide consisting of the amino acid sequence of SEQ ID NO:10, and a peptide consisting of the amino acid sequence of SEQ ID NO:11. More preferably, the MAGE-3 HLA class II-binding peptide is selected from the group consisting of a peptide consisting of the amino acid sequence of SEQ ID NO:3 and a peptide consisting of the amino acid sequence of SEQ ID NO:4.

According to yet another aspect of the invention, methods for treating a subject having a disorder characterized by expression of MAGE-3 are provided. The methods include administering to the subject an amount of an agent which enriches selectively in the subject the presence of complexes of an HLA class II molecule and a MAGE-3 HLA class II-binding peptide, sufficient to ameliorate the disorder. Preferably the HLA class II molecule is an HLA-DRB1/13 molecule, such as HLA-DRB1/1301 or HLA-DRB1/1302. In certain embodiments, the MAGE-3 HLA class II-binding peptide comprises the amino acid sequence of SEQ ID NO:11, or a functional variant thereof. Preferably the MAGE-3 HLA class II-binding peptide is selected from the group consisting of a peptide consisting of the amino acid sequence of SEQ ID NO:3, a peptide consisting of the amino acid sequence of SEQ ID NO:4, peptide consisting of the amino acid sequence of SEQ ID NO:9, peptide consisting of the amino acid sequence of SEQ ID NO:10, and a peptide consisting of the amino acid sequence of SEQ ID NO:11. More preferably, the MAGE-3 HLA class II-binding peptide is selected from the group consisting of a peptide consisting of the amino acid sequence of SEQ ID NO:3 and a peptide consisting of the amino acid sequence of SEQ ID NO:4.

Additional methods for treating a subject having a disorder characterized by expression of MAGE-3 are provided in another aspect of the invention. The methods include administering to the subject an amount of autologous CD4+ T lymphocytes sufficient to ameliorate the disorder, wherein the CD4+ T lymphocytes are specific for complexes of an HLA class II molecule and a MAGE-3 HLA class II-binding peptide. Preferably the HLA class II molecule is an HLA-DRB1/13 molecule, such as HLA-DRB1/1301 or HLA-DRB1/1302. In certain embodiments, the MAGE-3 HLA class II-binding peptide comprises the amino acid sequence of SEQ ID NO:11, or a functional variant thereof. Preferably the MAGE-3 HLA class II-binding peptide is selected from the group consisting of a peptide consisting of the amino acid sequence of SEQ ID NO:3, a peptide consisting of the amino acid sequence of SEQ ID NO:4, peptide consisting of the amino acid sequence of SEQ ID NO:9, peptide consisting of the amino acid sequence of SEQ ID NO:10, and a peptide consisting of the amino acid sequence of SEQ ID NO:11. More preferably, the MAGE-3 HLA class II-binding peptide is selected from the group consisting of a peptide consisting of the amino acid sequence of SEQ ID NO:3 and a peptide consisting of the amino acid sequence of SEQ ID NO:4.

According to another aspect of the invention, an isolated polypeptide is provided. The isolated polypeptide binds selectively a MAGE-3 HLA class II-binding peptide, provided that the isolated polypeptide is not an HLA class II molecule. In certain embodiments, the isolated polypeptide is an antibody and preferably is a monoclonal antibody. In other embodiments, the isolated polypeptide is an antibody fragment selected from the group consisting of a Fab fragment, a F(ab)$_2$ fragment or a fragment including a CDR3 region selective for a MAGE-3 HLA class II-binding peptide.

According to still another aspect of the invention, an isolated CD4+ T lymphocyte is provided. The isolated CD4+ T lymphocyte selectively binds a complex of an HLA class II molecule and a MAGE-3 HLA class II-binding peptide. Preferably the HLA class II molecule is an HLA-DRB1/13 molecule. In some embodiments the MAGE-3 HLA class II-binding peptide comprises the amino acid sequence of SEQ ID NO:11, or a functional variant thereof. Preferably the MAGE-3 HLA class II-binding peptide is selected from the group consisting of a peptide consisting of the amino acid sequence of SEQ ID NO:3, a peptide consisting of the amino acid sequence of SEQ ID NO:4, peptide consisting of the amino acid sequence of SEQ ID NO:9, peptide consisting of the amino acid sequence of SEQ ID NO:10, and a peptide consisting of the amino acid sequence of SEQ ID NO:11. More preferably, the MAGE-3 HLA class II-binding peptide is selected from the group consisting of a peptide consisting of the amino acid sequence of SEQ ID NO:3 and a peptide consisting of the amino acid sequence of SEQ ID NO:4.

According to still another aspect of the invention, an isolated antigen presenting cell is provided. The isolated antigen presenting cell comprises a complex of an HLA class II molecule and a MAGE-3 HLA class II-binding peptide. Preferably the HLA class II molecule is an HLA-DRB1/13 molecule. In certain embodiments the MAGE-3 HLA class II-binding peptide comprises the amino acid sequence of SEQ ID NO:11, or a functional variant thereof. In preferred embodiments the MAGE-3 HLA class II-binding peptide is selected from the group consisting of a peptide consisting of the amino acid sequence of SEQ ID NO:3, a peptide consisting of the amino acid sequence of SEQ ID NO:4, peptide consisting of the amino acid sequence of SEQ ID NO:9, peptide consisting of the amino acid sequence of SEQ ID NO:10, and a peptide consisting of the amino acid sequence of SEQ ID NO:11. More preferably, the MAGE-3 HLA class II-binding peptide is selected from the group consisting of a peptide consisting of the amino acid sequence of SEQ ID NO:3 and a peptide consisting of the amino acid sequence of SEQ ID NO:4.

Methods for identifying functional variants of a MAGE-3 HLA class II binding peptide are provided according to another aspect of the invention. According to the methods, a MAGE-3 HLA class II binding peptide, an HLA class II binding molecule which binds the MAGE-3 HLA class II binding peptide, and a T cell which is stimulated by the MAGE-3 HLA class II binding peptide presented by the HLA class II binding molecule are selected. A first amino acid residue of the MAGE-3 HLA class II binding peptide is mutated to prepare a variant peptide. The binding of the variant peptide to HLA class II binding molecule and stimulation of the T cell are then determined, wherein binding of the variant peptide to the HLA class II binding molecule and stimulation of the T cell by the variant peptide presented by the HLA class II binding molecule indicates that the variant peptide is a functional variant. In preferred embodiments, the MAGE-3 HLA class II binding peptide comprises the amino acid sequence of SEQ ID NO:11. More preferably, the peptide consists of the amino acid sequence of SEQ ID NO:3, SEQ ID NO:4, SEQ ID NO:9, SEQ ID NO:10, or SEQ ID NO:11. In certain embodiments, the methods further include the step of comparing the stimulation of the T cell by the MAGE-3 HLA class II binding peptide and the stimulation of the T cell by the functional variant as a determination of the effectiveness of the stimulation of the T cell by the functional variant.

The invention also provides pharmaceutical preparations containing any one or more of the medicaments described above or throughout the specification. Such pharmaceutical preparations can include pharmaceutically acceptable diluent carriers or excipients.

These and other objects of the invention will be described in further detail in connection with the detailed description of the invention.

BRIEF DESCRIPTION OF THE SEQUENCES

Figure 1:
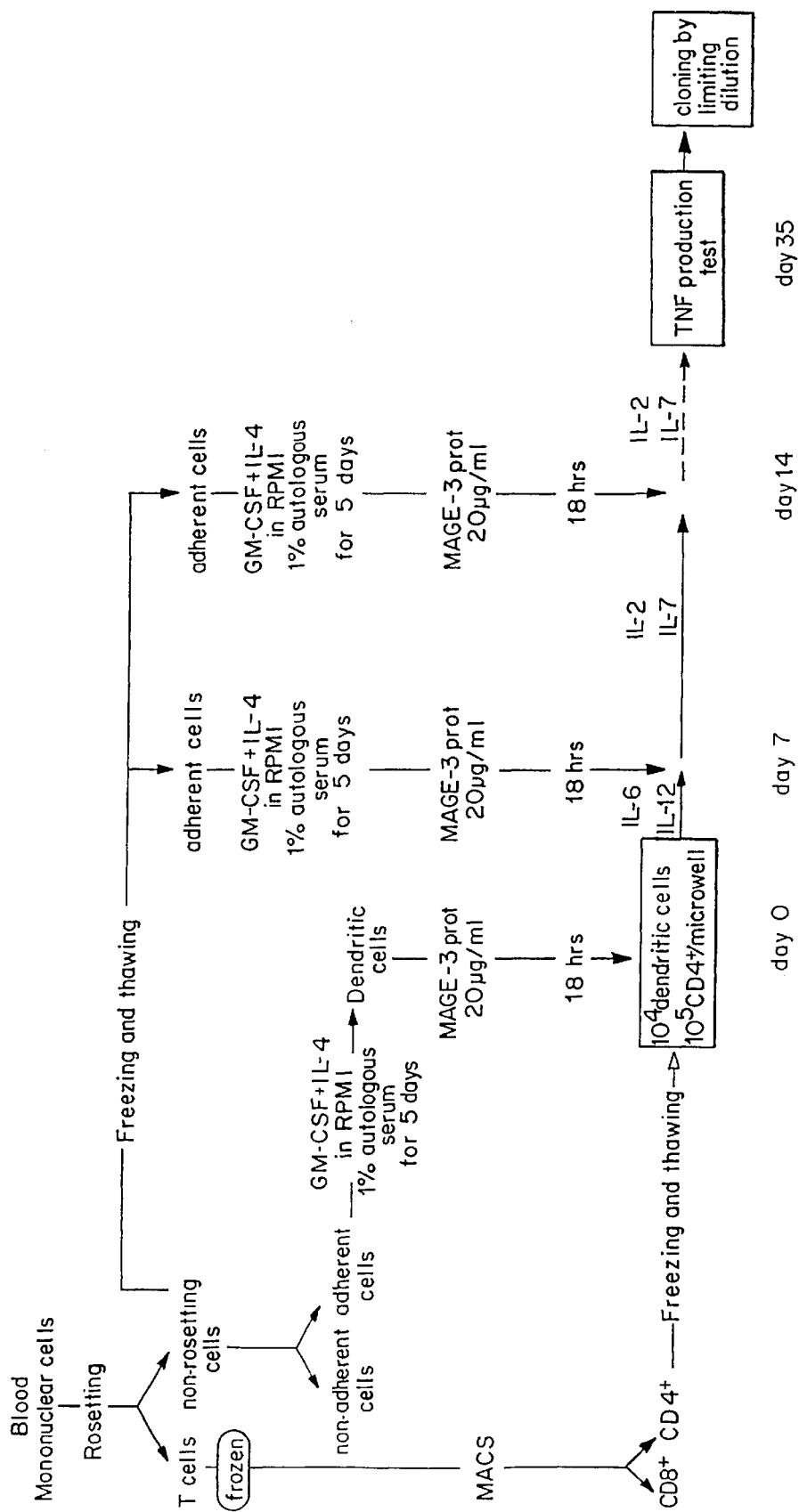
FIG. 1 is a schematic representation of the protocol used to obtain CD4 T cell lines specific for MAGE-3.

SEQ ID NO:1 is the nucleotide sequence of the MAGE-3 gene.

SEQ ID NO:2 is the amino acid sequence of the MAGE-3 protein.

SEQ ID NO:3 is the amino acid sequence of a peptide (MAGE-3 amino acids 111–126).

SEQ ID NO:4 is the amino acid sequence of a peptide (MAGE-3 amino acids 115–130).

SEQ ID NO:5 is the amino acid sequence of a peptide (MAGE-3 amino acids 127–142).

SEQ ID NO:6 is the amino acid sequence of a peptide (MAGE-3 amino acids 159–174).

SEQ ID NO:7 is the amino acid sequence of a peptide (MAGE-3 amino acids 116–123).

SEQ ID NO:8 is the amino acid sequence of a peptide (MAGE-3 amino acids 115–123).

SEQ ID NO:9 is the amino acid sequence of a peptide (MAGE-3 amino acids 115–126).

SEQ ID NO:10 is the amino acid sequence of a peptide (MAGE-3 amino acids 16–126).

SEQ ID NO:11 is the amino acid sequence of a peptide (MAGE-3 amino acids 1157–126).

SEQ ID NO:12 is the amino acid sequence of a peptide (MAGE-3 amino acids 118–126).

SEQ ID NO:13 is the nucleotide sequence of a nucleic acid encoding MAGE-3 amino acids 117–126.

DETAILED DESCRIPTION OF THE INVENTION

The invention provides isolated MAGE-3 peptides presented by HLA class II molecules, which peptides stimulate the proliferation and activation of CD4$^+$ T lymphocytes. Such peptides are referred to herein as "MAGE-3 HLA class II binding peptides" and "HLA class II binding peptides". Hence, one aspect of the invention is an isolated peptide which includes the amino acid sequence of SEQ ID NO:11.

The examples below show the isolation of peptides which are MAGE-3 HLA class II binding peptides. These exemplary peptides are processed translation products of the nucleic acid of SEQ ID NO:1. As such, it will be appreciated by one of ordinary skill in the art that the translation products from which a MAGE-3 HLA class II binding peptide is processed to a final form for presentation may be of any length or sequence so long as they encompass the MAGE-3 HLA class II binding peptide. As demonstrated in the examples below, peptides or proteins as small as 10 amino acids and as large as the amino acid sequence of the MAGE-3 protein (SEQ ID NO:2) are appropriately processed, presented by HLA class II molecules and effective in stimulating CD4$^+$ T lymphocytes. The peptide of SEQ ID NO:11 may have one, two, three, four, five, six, seven, eight, nine, ten, or more amino acids added to either or both ends. The antigenic portion of such a peptide is cleaved out under physiological conditions for presentation by HLA class II molecules.

As noted above, the invention embraces functional variants of the MAGE-3 HLA class II binding peptide. As used herein, a "functional variant" or "variant" of a MAGE-3 HLA class II binding peptide is a peptide which contains one or more modifications to the primary amino acid sequence of a MAGE-3 HLA class II binding peptide and retains the HLA class II and T cell receptor binding properties disclosed herein. Modifications which create a MAGE-3 HLA class II binding peptide functional variant can be made for example 1) to enhance a property of a MAGE-3 HLA class II binding peptide, such as peptide stability in an expression system or the stability of protein-protein binding such as HLA-peptide binding; 2) to provide a novel activity or property to a MAGE-3 HLA class II binding peptide, such as addition of an antigenic epitope or addition of a detectable moiety; or 3) to provide a different amino acid sequence that produces the same or similar T cell stimulatory properties. Modifications to a MAGE-3 HLA class II binding peptide can be made to a nucleic acid which encodes the peptide, and can include deletions, point mutations, truncations, amino acid substitutions and additions of amino acids. Alternatively, modifications can be made directly to the polypeptide, such as by cleavage, addition of a linker molecule, addition of a detectable moiety, such as biotin, addition of a fatty acid, substitution of one amino acid for another and the like. Modifications also embrace fusion proteins comprising all or part of the MAGE-3 HLA class II binding peptide amino acid sequence.

The amino acid sequence of MAGE-3 HLA class II binding peptides may be of natural or non-natural origin, that is, they may comprise a natural MAGE-3 HLA class II binding peptide molecule or may comprise a modified sequence as long as the amino acid sequence retains the ability to stimulate helper T cells when presented and retains the property of binding to an HLA class II molecule such as an HLA DRB1/13 molecule. For example, MAGE-3 HLA class II binding peptides in this context may be fusion proteins of a MAGE-3 HLA class II binding peptide and unrelated amino acid sequences, synthetic peptides of amino acid sequences shown in SEQ ID Nos:3, 4, 9, 10 and 11, labeled peptides, peptides isolated from patients with a MAGE-3 expressing cancer, peptides isolated from cultured cells which express MAGE-3, peptides coupled to nonpeptide molecules (for example in certain drug delivery systems) and other molecules which include the amino acid sequence of SEQ ID NO:11.

Preferably, MAGE-3 HLA class II binding peptides are non-hydrolyzable. To provide such peptides, one may select MAGE-3 HLA class II binding peptides from a library of non-hydrolyzable peptides, such as peptides containing one or more D-amino acids or peptides containing one or more non-hydrolyzable peptide bonds linking amino acids. Alternatively, one can select peptides which are optimal for inducing CD4+ T lymphocytes and then modify such peptides as necessary to reduce the potential for hydrolysis by proteases. For example, to determine the susceptibility to proteolytic cleavage, peptides may be labeled and incubated with cell extracts or purified proteases and then isolated to determine which peptide bonds are susceptible to proteolysis, e.g., by sequencing peptides and proteolytic fragments. Alternatively, potentially susceptible peptide bonds can be identified by comparing the amino acid sequence of a MAGE-3 HLA class II binding peptide with the known cleavage site specificity of a panel of proteases. Based on the results of such assays, individual peptide bonds which are susceptible to proteolysis can be replaced with non-hydrolyzable peptide bonds by in vitro synthesis of the peptide.

Many non-hydrolyzable peptide bonds are known in the art, along with procedures for synthesis of peptides containing such bonds. Non-hydrolyzable bonds include -psi[$CH_2NH$]-reduced amide peptide bonds, -psi[$COCH_2$]-ketomethylene peptide bonds, -psi[CH(CN)NH]-(cyanomethylene)amino peptide bonds, -psi[$CH_2CH(OH)$]-hydroxyethylene peptide bonds, -psi[$CH_2O$]-peptide bonds, and -psi[$CH_2S$]-thiomethylene peptide bonds.

Nonpeptide analogs of peptides, e.g., those which provide a stabilized structure or lessened biodegradation, are also contemplated. Peptide mimetic analogs can be prepared based on a selected MAGE-3 HLA class II binding peptide by replacement of one or more residues by nonpeptide moieties. Preferably, the nonpeptide moieties permit the peptide to retain its natural confirmation, or stabilize a preferred, e.g., bioactive, confirmation. One example of methods for preparation of nonpeptide mimetic analogs from peptides is described in Nachman et al., Regul. Pept. 57:359–370 (1995). Peptide as used herein embraces all of the foregoing.

If a variant involves a change to an amino acid of SEQ ID NO:3, SEQ ID NO:4, SEQ ID NO:9, SEQ ID NO:10 or SEQ ID NO:11, functional variants of the MAGE-3 HLA class II binding peptide having conservative amino acid substitutions typically will be preferred, i.e., substitutions which retain a property of the original amino acid such as charge, hydrophobicity, conformation, etc. Examples of conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Other methods for identifying functional variants of the MAGE-3 HLA class II binding peptides are provided in a published PCT application of Strominger and Wucherpfennig (U.S. Pat. No. 96/03 182). These methods rely upon the development of amino acid sequence motifs to which potential epitopes may be compared. Each motif describes a finite set of amino acid sequences in which the residues at each (relative) position may be (a) restricted to a single residue, (b) allowed to vary amongst a restricted set of residues, or (c) allowed to vary amongst all possible residues. For example, a motif might specify that the residue at a first position may be any one of the residues valine, leucine, isoleucine, methionine, or phenylalanine; that the residue at the second position must be histidine; that the residue at the third position may be any amino acid residue; that the residue at the fourth position may be any one of the residues valine, leucine, isoleucine, methionine, phenylalanine, tyrosine or tryptophan; and that the residue at the fifth position must be lysine.

Sequence motifs for MAGE-3 HLA class II binding peptide functional variants can be developed by analysis of the binding domains or binding pockets of major histocompatibility complex HLA-DR proteins and/or the T cell receptor ("TCR") contact points of the MAGE-3 HLA class II binding peptides disclosed herein. By providing a detailed structural analysis of the residues involved in forming the HLA class II binding pockets, one is enabled to make predictions of sequence motifs for binding to any of the HLA class II proteins.

Using these sequence motifs as search, evaluation, or design criteria, one is enabled to identify classes of peptides (functional variants of the MAGE-3 HLA class II binding peptides disclosed herein) which have a reasonable likelihood of binding to a particular HLA molecule and of interacting with a T cell receptor to induce T cell response. These peptides can be synthesized and tested for activity as described herein. Use of these motifs, as opposed to pure sequence homology (which excludes many peptides which are antigenically similar but quite distinct in sequence) or sequence homology with unlimited "conservative" substitutions (which admits many peptides which differ at critical highly conserved sites), represents a method by which one of ordinary skill in the art can evaluate peptides for potential application in the treatment of disease.

The Strominger and Wucherpfennig PCT application, and references cited therein, all of which are incorporated by reference, describe the HLA class II and TCR binding pockets which contact residues of an HLA class II peptide.

By keeping the residues which are likely to bind in the HLA class II and/or TCR binding pockets constant or permitting only specified substitutions, functional variants of the MAGE-3 HLA class II binding peptides can be prepared which retain binding to HLA class II and T cell receptor.

Thus methods for identifying functional variants of a MAGE-3 HLA class II binding peptide are provided. In general, the methods include selecting a MAGE-3 HLA class II binding peptide, an HLA class II binding molecule which binds the MAGE-3 HLA class II binding peptide, and a T cell which is stimulated by the MAGE-3 HLA class II binding peptide presented by the HLA class II binding molecule. In preferred embodiments, the MAGE-3 HLA class II binding peptide comprises the amino acid sequence of SEQ ID NO:11. More preferably, the peptide consists of the amino acid sequence of SEQ ID NO:3, SEQ ID NO:4, SEQ ID NO:9, SEQ ID NO:10, or SEQ ID NO:11. A first amino acid residue of the MAGE-3 HLA class II binding peptide is mutated to prepare a variant peptide. The amino acid residue can be mutated according to the principles of HLA and T cell receptor contact points set forth in the Strominger and Wucherpfennig PCT application described above. Any method for preparing variant peptides can be employed, such as synthesis of the variant peptide, recombinantly producing the variant peptide using a mutated nucleic acid molecule, and the like.

The binding of the variant peptide to HLA class II binding molecule and stimulation of the T cell are then determined according to standard procedures. For example, as exemplified below, the variant peptide can be contacted with an antigen presenting cell which contains the HLA class II molecule which binds the MAGE-3 peptide to form a complex of the variant peptide and antigen presenting cell. This complex can then be contacted with a T cell which recognizes the MAGE-3 HLA class II binding peptide presented by the HLA class II binding molecule. T cells can be obtained from a patient having a condition characterized by expression of MAGE-3. Recognition of variant peptides by the T cells can be determined by measuring an indicator of T cell stimulation such as TNF or IFNγ production.

Binding of the variant peptide to the HLA class II binding molecule and stimulation of the T cell by the variant peptide presented by the HLA class II binding molecule indicates that the variant peptide is a functional variant. The methods also can include the step of comparing the stimulation of the T cell by the MAGE-3 HLA class II binding peptide and the stimulation of the T cell by the functional variant as a determination of the effectiveness of the stimulation of the T cell by the functional variant. By comparing the functional variant with the MAGE-3 HLA class II binding peptide, peptides with increased T cell stimulatory properties can be prepared.

Variants of the MAGE-3 HLA class II binding peptides prepared by any of the foregoing methods can be sequenced, if necessary, to determine the amino acid sequence and thus deduce the nucleotide sequence which encodes such variants.

Also a part of the invention are those nucleic acid sequences which code for a MAGE-3 HLA class II binding peptide or variant thereof and other nucleic acid sequences which hybridize to a nucleic acid molecule consisting of the above described nucleotide sequences, under stringent conditions. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers to hybridization at 65° C. in hybridization buffer (3.5×SSC, 0.02% Ficoll, 0.02% Polyvinyl pyrolidone, 0.02% Bovine Serum Albumin, 25 mM $NaH_2PO_4$ (pH7), 0.5% SDS, 2 mM EDTA). SSC is 0.15M Sodium Chloride/0.15M Sodium Citrate, pH 7; SDS is Sodium Dodecyl Sulphate; and EDTA is Ethylene diaminetetraacetic acid. After hybridization, the membrane upon which the DNA is transferred is washed at 2×SSC at room temperature and then at 0.1×SSC/0.1×SDS at 65° C.

There are other conditions, reagents, and so forth which can used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of nucleic acids encoding the MAGE-3 HLA class II binding peptides of the invention. The skilled artisan also is familiar with the methodology for screening cells and libraries for expression of such molecules which then are routinely isolated, followed by isolation of the pertinent nucleic acid molecule and sequencing.

In general homologs and alleles typically will share at least 50% amino acid identity and/or at least 40% nucleotide identity to the amino acid sequence of a MAGE-3 HLA class II binding peptide (such as SEQ ID NOs:3, 4, 9, 10 or 11) or nucleic acids which encode such a peptide, respectively. In some instances homologs and alleles will share at least 50% nucleotide identity and/or at least 65% amino acid identity and in still other instances will share at least 60% nucleotide identity and/or at least 75% amino acid identity. Complements of the foregoing nucleic acids also are embraced by the invention.

In screening for nucleic acids which encode a MAGE-3 HLA class II binding peptide, a nucleic acid hybridization such as a Southern blot or a Northern blot may be performed using the foregoing conditions, together with a $^{32}P$ probe. After washing the membrane to which DNA encoding a MAGE-3 HLA class II binding peptide was finally transferred, the membrane can be placed against X-ray film to detect the radioactive signal.

The invention also includes the use of nucleic acid sequences which include alternative codons that encode the same amino acid residues of the MAGE-3 HLA class II binding peptides. For example, as disclosed herein, the peptide RKVAELVHFLLLKYRA (SEQ ID NO:3) is a MAGE-3 HLA class II binding peptide. The leucine residues (amino acids No. 6, 10, 11 and 12 of SEQ ID NO:3) can be encoded by the codons CUA, CUC, CUG, CUU, UUA and UUG. Each of the six codons is equivalent for the purposes of encoding a leucine residue. Thus, it will be apparent to one of ordinary skill in the art that any of the leucine-encoding nucleotide triplets may be employed to direct the protein synthesis apparatus, in vitro or in vivo, to incorporate a leucine residue. Similarly, nucleotide sequence triplets which encode other amino acid residues comprising the MAGE-3 HLA class II binding peptide of SEQ ID NO:3 include: CGA, CGC, CGG, CGT, AGA and AGG (arginine codons); AAA and AAG (lysine codons); GUA, GUC, GUG and GUU (valine codons); GAA and GAG (glutamine codons); CAC and CAU (histidine codons); UUC and UUU (phenylalanine codons) and UAC and UAU (tyrosine codons). Other amino acid residues may be encoded similarly by multiple nucleotide sequences. Thus, the invention embraces degenerate nucleic acids that differ from the native MAGE-3 HLA class II binding peptide encoding nucleic acids in codon sequence due to the degeneracy of the genetic code.

It will also be understood that the invention embraces the use of the sequences in expression vectors, as well as to transfect host cells and cell lines, be these prokaryotic (e.g., E. coli), or eukaryotic (e.g., dendritic cells, CHO cells, COS cells, yeast expression systems and recombinant baculovirus expression in insect cells). The expression vectors require that the pertinent sequence, i.e., those described supra, be operably linked to a promoter. As it has been found that human HLA-DRB1/1302 molecules present a MAGE-3 HLA class II binding peptide, the expression vector may also include a nucleic acid sequence coding for an HLA-DRB1/13 molecule. In a situation where the vector contains both coding sequences, it can be used to transfect a cell which does not normally express either one. The MAGE-3 HLA class II binding peptide coding sequence may be used alone, when, e.g. the host cell already expresses an HLA-DRB1/13 molecule. Of course, there is no limit on the particular host cell which can be used as the vectors which contain the two coding sequences may be used in host cells which do not express HLA-DRB1/13 molecules if desired, and the nucleic acid coding for the MAGE-3 HLA class II binding peptide can be used in antigen presenting cells which express an HLA-DRB1/13 molecule. As used herein, "an HLA-DRB1/13 molecule" includes the subtypes DRB1*1301, DRB1*1302, DRB1*13031, DRB1*13032, DRB1*1304, DRB1*1305, DRB1*1306, DRB1*1307, DRB1*1308, DRB1*1309, DRB1*1310, DRB1*1311, DRB1*1312, DRB1*1314, DRB1*1315, DRB1*1316, DRB1*1317, DRB1*1318, DRB1*1319, DRB1*1320, DRB1*1321, DRB1*1322, DRB1*1323 and DRB1*1324.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

Preferably the expression vectors contain sequences which target MAGE-3 or a MAGE-3 HLA class II binding peptide to the endosomes of a cell in which the protein or peptide is expressed. HLA class II molecules contain an invariant chain (Ii) which impedes binding to other molecules to the HLA class II molecules. This invariant chain is cleaved in endosomes, thereby permitting binding of peptides by HLA class II molecules. Therefore it is preferable that the MAGE-3 HLA class II binding peptides and precursors thereof (e.g. the MAGE-3 protein) are targeted to the endosome, thereby enhancing MAGE-3 HLA class II binding peptide binding to HLA class II molecules. Targeting signals for directing molecules to endosomes are known in the art and these signals conveniently can be incorporated in expression vectors such that fusion proteins which contain the endosomal targeting signal are produced. Sanderson et al. (Proc. Nat'l Acad. Sci. USA 92:7217–7221, 1995) and Wu et al. (Proc. Nat'l Acad. Sci. USA 92:11671–11675, 1995) describe endosomal targeting signals (invariant chain Ii and lysosomal-associated membrane protein LAMP-1, respectively) and their use in directing antigens to endosomal and or lysosomal cellular compartments.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Especially, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding a MAGE-3 HLA class II binding peptide. That heterologous DNA (RNA) is placed under operable control of transcriptional elements to permit the expression of the heterologous DNA in the host cell.

Preferred systems for mRNA expression in mammalian cells are those such as pRc/CMV (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710–4716, 1996). Still another preferred expression vector is an adenovirus, described by Stratford-Perricaudet, which is defective for E1 and E3 proteins (*J. Clin. Invest.* 90:626–630, 1992). The use of the adenovirus as an Adeno.P1A recombinant is disclosed by Wamier et al., in intradermal injection in mice for immunization against P1A (*Int. J. Cancer*, 67:303–310, 1996).

The invention also embraces so-called expression kits, which allow the artisan to prepare a desired expression vector or vectors. Such expression kits include at least separate portions of at least two of the previously discussed materials. Other components may be added, as desired.

The invention as described herein has a number of uses, some of which are described herein. First, the invention permits the artisan to diagnose a disorder characterized by expression of a MAGE-3 HLA class II binding peptide. These methods involve determining expression of a MAGE-3 HLA class II binding peptide, or a complex of a MAGE-3 HLA class II binding peptide and an HLA class II molecule in a biological sample. The expression of a peptide or complex of peptide and HLA class II molecule can be determined by assaying with a binding partner for the peptide or complex, such as an antibody.

The invention also permits the artisan to treat a subject having a disorder characterized by expression of a MAGE-3 HLA class II binding peptide. Treatments include administering an agent which enriches in the subject a complex of a MAGE-3 HLA class II binding peptide and an HLA class II molecule, and administering CD4$^+$ T lymphocytes which are specific for such complexes. Agents useful in the foregoing treatments include MAGE-3 HLA class II binding peptides and functional variants thereof, complexes of such peptides and HLA class II binding molecules (e.g. HLA DRB1/1302), antigen presenting cells bearing complexes of a MAGE-3 HLA class II binding peptide and an HLA class II binding molecule, and the like. The invention also permits an artisan to selectively enrich a population of T lymphocytes for CD4$^+$ T lymphocytes specific for a MAGE-3 HLA class II binding peptide.

The isolation of the MAGE-3 HLA class II binding peptides also makes it possible to isolate nucleic acids which encode the MAGE-3 HLA class II binding peptides. Nucleic acids can be used to produce in vitro or in prokaryotic or eukaryotic host cells the MAGE-3 HLA class II binding peptides. A variety of methodologies well-known to the skilled practitioner can be utilized to obtain isolated MAGE-3 HLA class II binding peptides. For example, an expression vector may be introduced into cells to cause production of the peptides. In another method, mRNA transcripts may be microinjected or otherwise introduced into cells to cause production of the encoded peptides. Translation of mRNA in cell-free extracts such as the reticulocyte lysate system also may be used to produce peptides. Peptides comprising the MAGE-3 HLA class II binding peptide of the invention may also be synthesized in vitro. Those skilled in the art also can readily follow known methods for isolating peptides in order to obtain isolated MAGE-3 HLA class II binding peptides. These include, but are not limited to, immunochromotography, HPLC, size-exclusion chromatography, ion-exchange chromatography and immune-affinity chromatography. These isolated MAGE-3 HLA class II binding peptides, or complexes of the peptides and HLA class II molecules, such as an HLA-DRB1/13 molecule, may be combined with materials such as adjuvants to produce vaccines useful in treating disorders characterized by expression of the MAGE-3 HLA class II binding peptide. In addition, vaccines can be prepared from cells which present the MAGE-3 HLA class II binding peptide/HLA complexes on their surface, such as dendritic cells, B cells, non-proliferative transfectants, etcetera. In all cases where cells are used as a vaccine, these can be cells transfected with coding sequences for one or both of the components necessary to stimulate CD4$^+$ lymphocytes, or be cells which already express both molecules without the need for transfection. Vaccines also encompass naked DNA or RNA, encoding a MAGE-3 HLA class II binding peptide or precursor thereof, which may be produced in vitro and administered via injection, particle bombardment, nasal aspiration and other methods. Vaccines of the "naked nucleic acid" type have been demonstrated to provoke an immunological response including generation of CTLs specific for the peptide encoded by the naked nucleic acid (*Science* 259:1745–1748, 1993).

The MAGE-3 HLA class II binding peptide, as well as complexes of MAGE-3 HLA class II binding peptide and HLA molecule, also may be used to produce antibodies, using standard techniques well known to the art. Standard reference works setting forth the general principles of antibody production include Catty, D., *Antibodies. A Practical Approach*, Vol. 1, IRL Press, Washington D.C. (1988); Klein, J., *Immunology: The Science of Cell-Non-Cell Discrimination*, John Wiley and Sons, New York (1982); Kennett, R., et al., *Monoclonal Antibodies. Hybridoma. A New Dimension In Biological Analyses*, Plenum Press, New York (1980); Campbell, A., *Monoclonal Antibody Technology*, in *Laboratory Techniques and Biochemistry and Molecular Biology*, Vol. 13 (Burdon, R. et al. EDS.), Elsevier Amsterdam (1984); and Eisen, H. N.,*Microbiology*, third edition, Davis, B. D. et al. EDS. (Harper & Rowe, Philadelphia (1980).

The antibodies of the present invention thus are prepared by any of a variety of methods, including administering protein, fragments of protein, cells expressing the protein or fragments thereof and an appropriate HLA class II molecule, and the like to an animal to induce polyclonal antibodies. The production of monoclonal antibodies is according to techniques well known in the art. As detailed herein, such antibodies may be used for example to identify tissues expressing protein or to purify protein. Antibodies also may be coupled to specific labeling agents for imaging or to antitumor agents, including, but not limited to, methotrexate, radioiodinated compounds, toxins such as ricin, other cytostatic or cytolytic drugs, and so forth.

Antibodies prepared according to the invention also preferably are specific for the peptide/HLA complexes described herein.

When "disorder" or "condition" is used herein, it refers to any pathological condition where the MAGE-3 HLA class II binding peptide is expressed. Such disorders include cancers, such as melanomas, squamous cell carcinomas of the head, neck, lung or esophagus, colorectal carcinomas, osteosarcomas, neuroblastomas, non-squamous cell carcinomas of the head or neck, ovarian tumors, lymphocytic leukemias, bladder carcinomas, prostate carcinomas, etc.

Some therapeutic approaches based upon the disclosure are premised on inducing a response by a subject's immune system to MAGE-3 HLA class II binding peptide presenting cells. One such approach is the administration of autologous CD4+ T cells specific to the complex of MAGE-3 HLA class II binding peptide and an HLA class II molecule to a subject with abnormal cells of the phenotype at issue. It is within the skill of the artisan to develop such CD4+ T cells in vitro. Generally, a sample of cells taken from a subject, such as blood cells, are contacted with a cell presenting the complex and capable of provoking CD4+ T lymphocytes to proliferate. The target cell can be a transfectant, such as a COS cell, or an antigen presenting cell bearing HLA class II, such as dendritic cells or B cells. These transfectants present the desired complex of their surface and, when combined with a CD4+ T lymphocyte of interest, stimulate its proliferation. COS cells, such as those used herein are widely available, as are other suitable host cells. Specific production of a CD4+ T lymphocytes is described below. The clonally expanded autologous CD4+ T lymphocytes then are administered to the subject. The CD4+ T lymphocytes then stimulate the subject's immune response, thereby achieving the desired therapeutic goal.

The foregoing therapy assumes that at least some of the subject's abnormal cells present the relevant HLA/peptide complex. This can be determined very easily, as the art is very familiar with methods for identifying cells which present a particular HLA molecule, as well as how to identify cells expressing DNA of the pertinent sequences, in this case a MAGE-3 sequence.

The foregoing therapy is not the only form of therapy that is available in accordance with the invention. CD4+ T lymphocytes can also be provoked in vivo, using a number of approaches. One approach is the use of non-proliferative cells expressing the complex. The cells used in this approach may be those that normally express the complex, such as dendritic cells or cells transfected with one or both of the genes necessary for presentation of the complex. Chen et al., (*Proc. Natl. Acad. Sci. USA* 88: 110–114, 1991) exemplifies this approach, showing the use of transfected cells expressing HPV-E7 peptides in a therapeutic regime. Various cell types may be used. Similarly, vectors carrying one or both of the genes of interest may be used. Viral or bacterial vectors are especially preferred. For example, nucleic acids which encode a MAGE-3 HLA class II binding peptide may be operably linked to promoter and enhancer sequences which direct expression of the MAGE-3 HLA class II binding peptide in certain tissues or cell types. The nucleic acid may be incorporated into an expression vector. Expression vectors may be unmodified extrachromosomal nucleic acids, plasmids or viral genomes constructed or modified to enable insertion of exogenous nucleic acids, such as those encoding MAGE-3 HLA class II binding peptides. Nucleic acids encoding a MAGE-3 HLA class II binding peptide also may be inserted into a retroviral genome, thereby facilitating integration of the nucleic acid into the genome of the target tissue or cell type. In these systems, the gene of interest is carried by a microorganism, e.g., a Vaccinia virus, retrovirus or the bacteria BCG, and the materials de facto "infect" host cells. The cells which result present the complex of interest, and are recognized by autologous CD4+ T cells, which then proliferate.

A similar effect can be achieved by combining a MAGE-3 HLA class II binding peptide with an adjuvant to facilitate incorporation into HLA class II presenting cells in vivo. If larger than the HLA class II binding portion, the MAGE-3 HLA class II binding peptide can be processed if necessary to yield the peptide partner of the HLA molecule while the TRA is presented without the need for further processing. Generally, subjects can receive an intradermal injection of an effective amount of the MAGE-3 HLA class II binding peptide. Initial doses can be followed by booster doses, following immunization protocols standard in the art.

Any of the foregoing compositions or protocols can include also MAGE-3 HLA class I binding peptides for induction of a cytolytic T lymphocyte response. Several such peptides have been described in U. S. Pat. Nos. 5,585,461 and 5,591,430 as well as by Gaugler et al. (*J. Exp. Med.* 179:921–930, 1994), van der Bruggen et al. (*Eur. J. Immonol.* 24:3038–3043, 1994), and Herman et al. (*Immunogenetics* 43:377–383, 1996). By administering MAGE-3 peptides which bind HLA class I and class II molecules (or nucleic acid encoding such peptides), an improved immune response may be provided by inducing both T helper cells and T killer cells.

As part of the immunization protocols, substances which potentiate the immune response may be administered with nucleic acid or peptide components of a cancer vaccine. Such immune response potentiating compound may be classified as either adjuvants or cytokines. Adjuvants may enhance the immunological response by providing a reservoir of antigen (extracellularly or within macrophages), activating macrophages and stimulating specific sets of lymphocytes. Adjuvants of many kinds are well known in the art; specific examples include MPL (SmithKline Beecham), a congener obtained after purification and acid hydrolysis of *Salmonella minnesota* Re 595 lipopolysaccharide, QS21 (SmithKline Beecham), a pure QA-21 saponin purified from *Quillja saponaria* extract, and various water-in-oil emulsions prepared from biodegradable oils such as squalene and/or tocopherol. Cytokines are also useful in vaccination protocols as a result of lymphocyte stimulatory properties. Many cytokines useful for such purposes will be known to one of ordinary skill in the art, including interleukin-12 (IL-12) which has been shown to enhance the protective effects of vaccines (*Science* 268: 1432–1434, 1995).

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents.

The preparations of the invention are administered in effective amounts. An effective amount is that amount of a pharmaceutical preparation that alone, or together with further doses, stimulates the desired response. In the case of treating cancer, the desired response is inhibiting the progression of the cancer. This may involve only slowing the progression of the disease temporarily, although more preferably, it involves halting the progression of the disease permanently. In the case of inducing an immune response, the desired response is an increase in antibodies or T lymphocytes which are specific for the MAGE-3 immunogen(s) employed. These desired responses can be monitored by routine methods or can be monitored according to diagnostic methods of the invention discussed herein.

Where it is desired to stimulate an immune response using a therapeutic composition of the invention, this may involve the stimulation of a humoral antibody response resulting in an increase in antibody titer in serum, a clonal expansion of cytotoxic lymphocytes, or some other desirable immunologic response. It is believed that doses of immunogens ranging from one nanogram/kilogram to 100 miligrams/kilogram, depending upon the mode of administration, would be effective. The preferred range is believed to be between 500 nanograms and 500 micrograms per kilogram. The absolute amount will depend upon a variety of factors, including the material selected for administration, whether the administration is in single or multiple doses, and individual patient parameters including age, physical condition, size, weight, and the stage of the disease. These factors are well known to those of ordinary skill in the art and can be addressed with no more than routine experimentation.

EXAMPLES

We have identified antigenic peptides encoded by gene MAGE-3 and presented to T cells in the context of HLA class II molecules. The strategy has consisted of loading dendritic cells of normal blood donors with a recombinant MAGE-3 protein and to use these antigen-presenting cells to induce in vitro the activation and proliferation of specific CD4 lymphocytes. The protocol is described below (A, B, C) and in FIG. 1.

A. Processing of Human Blood

Peripheral blood was obtained from the local blood bank (NON CANCER PATIENTS) as standard buffy coat preparations. Peripheral blood mononuclear cells (PBMC) were isolated by centriftigation on Lymphoprep (Nycomed Pharma, Oslo, Norway). In order to minimize contamination of PBMC by platelets, the preparation was first centrifuged for 20 min/1000 rpm at room temperature. After removal of the top 20–25 ml, containing most of the platelets, the tubes were centrifuged for 20 min/1500 rpm at room temperature. PBMC were depleted of T cells by rosetting with 2-aminoethylisothiouronium (Sigma) treated sheep erythrocytes. The lymphocyte-depleted PBMC were left to adhere for 2 hours at 37° C. in culture flasks (Falcon) at a density of $2 \times 10^6$ cells/ml in RPMI 1640 medium supplemented with L-asparagine (0.24 mM), L-arginine (0.55 mM), L-glutamine (1.5 mM) and 1% autologous serum (complete medium). Non-adherent cells were discarded and adherent cells were cultured in the presence of IL-4 (100 U/ml) and GM-CSF (100 ng/ml) in complete medium. Cultures were fed on day 2 and 4 by removing 5 ml of the medium and adding back fresh medium with IL-4 (100 U/ml) and GM-CSF (100 ng/ml). On day 5, the non-adherent cell population was used as a source of enriched dendritic cells.

Rosetted T cells were treated with $NH_4Cl$ (160 mM) to lyse the sheep erythrocytes, and washed. $CD4^+$ T lymphocytes were isolated from rosetted T cells by negative selection using an anti-CD8 monoclonal antibody coupled to magnetic microbeads (Miltenyi Biotech, Germany) by sorting through the Dynal magnet as recommended by the manufacturer.

B. Cytokines

Human recombinant IL-2 was donated by Biogen (Geneva, Switzerland). Human recombinant IL-4, IL-6 and IL-12 were obtained in our laboratory. Human recombinant IL-7 was purchased from Genzyme (Cambridge, Mass.). Human recombinant GM-CSF was donated from Sandoz (Sandoz Pharma, Basel, Switzerland). Human recombinant TNF-α was purchased from R & D Systems (Abigdon, UK).

C. Feeding with Protein and Mixed Lymphocyte-dendritic Cells Culture

The recombinant His-MAGE-3 protein (MAGE-3 with a His tag) was produced by Smith Kline Corporation Pharmaceutical Company (Rixensart, Belgium) in *E. coli* and purified by standard chromatographic procedures. Autologous dendritic cells were incubated at 37° C., 5% $CO_2$, for 18–20 hours in RPMI medium supplemented with 1% autologous serum, IL-4 (100 U/ml), GM-CSF (100 ng/ml) and TNF-α (1 ng/ml) in the presence of the recombinant His-MAGE-3 protein (20 µg/ml). His-MAGE-3 protein-pulsed dendritic cells were washed and added at $10^4$ per round-bottomed microwell to $10^5$ $CD4^+$ T lymphocytes in 200 µl Iscove's medium supplemented with 10% human serum, L-asparagine (0.24 mM), L-arginine (0.55 mM), L-glutamine (1.5 mM) in the presence of IL-6 (1000 U/ml) and IL-12 (10 ng/ml). The $CD4^+$ lymphocytes were weekly restimulated with autologous dendritic cells freshly pulsed with the His-MAGE-3 protein and were grown in culture medium supplemented with IL-2 (10 U/ml) and IL-7 (5 ng/ml).

Example 1

Obtention of CD4 T Cell Lines and Clones Specific for MAGE-3

Figure 2:
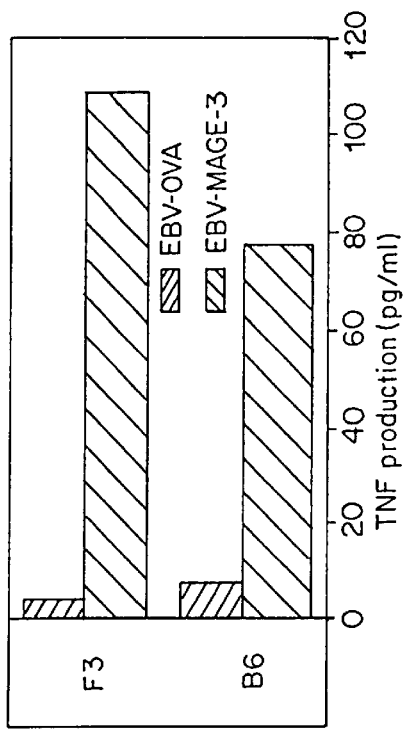
FIG. 2 is a graph showing CD4$^+$ T cell lines B6 and F3 recognized autologous EBV-B cells which have processed the recombinant His-MAGE-3 protein.

The microcultures that contained proliferating CD4 T cells were assessed 35 days after the start of the culture for their capacity to produce TNF when stimulated with autologous EBV-B cells pulsed with the His-MAGE-3 protein: autologous EBV-B cells were incubated for 18–20 hours in the presence of 20 µg/ml of His-MAGE-3 protein, or Ovalbumin (Sigma) as a negative control. EBV-B cells referred to herein are B cells which were immortalized with Epstein Barr virus. The EBV-B cells were prepared according to art-standard procedures. Protein-pulsed EBV-B cells were washed and added at 5,000 per round-bottomed microwell to 2,500 $CD4^+$ T lymphocytes in 150 µl of Iscove's medium supplemented with L-glutamine, L-arginine, L-asparagine, 10% human serum and IL-2 (25 U/ml). After 18–20 hours, supernatants were harvested and assessed for TNF contents by testing their toxicity for TNF-sensitive WEHI 164-13 cells as previously described. The CD4+ T cell lines producing TNF specifically (FIG. 2) were cloned by limiting dilution, using the autologous EBV-B cell line pulsed with exogenous His-MAGE-3 protein as stimulating cells and allogeneic EBV-B cells (LG2-EBV) as feeder cells. CD4 T cell clones were maintained in culture by weekly restimulation with autologous EBV-B cells pulsed with the His-MAGE-3 protein and LG2-EBV in culture medium supplemented with 50 U/ml of IL-2.

Figure 3:
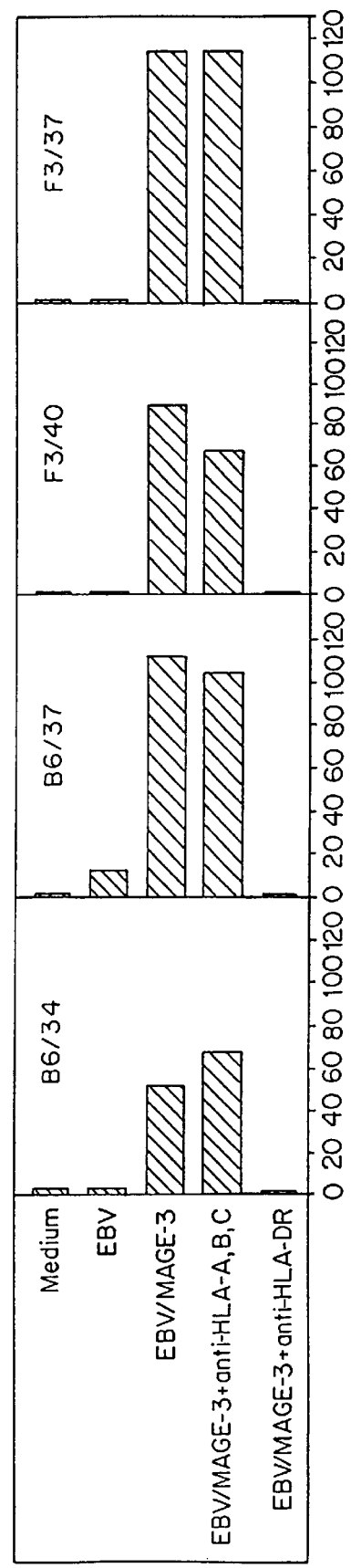
FIG. 3 is a graph showing that the recognition by CD4$^+$ T cell clones of autologous EBV-B cells pulsed with exogenous His-MAGE-3 protein is inhibited by an anti-HLA DR monoclonal antibody.

CD4 T cell clones were tested for specificity on autologous EBV-B cells pulsed with the exogenous His-MAGE-3 protein: EBV-B cells (500,000/ml) were incubated 18–20 hours at 37° C. in the presence 20 µg/ml of the MAGE-3 recombinant protein. Protein-pulsed EBV-B cells were washed and added at 5,000 per round-bottomed microwell to 2,500 CD4+ T lymphocytes in 150 µl of Iscove's medium supplemented with L-glutamine, L-arginine, L-asparagine, 10% human serum and IL-2 (25 U/ml). After 18–20 hours, supernatants were harvested and assessed for TNF and IFN-65 secretion. IFN-γ production was measured using an ELISA assay developed in our laboratory with reagents from Medgenix Diagnostics-Biosource (Fleurus, Belgium). Briefly, the assay was a standard ELISA in which IFN-γ antibodies were coated onto the wells of plastic microtiter plates prior to incubation with cell supernatants to determine the amount of IFN-γ produced. Any IFN-γ ELISA assay could be used to measure IFN-γ produced. Several MAGE-3 specific clones were obtained from the B6 line (FIG. 3).

The MAGE-3 epitope is presented to the CD4 clones by HLA-DR molecules (FIG. 3): MAGE-3-pulsed EBV-B cells were cocultured for 24 hours at 37° C. under 8% $CO_2$ with MAGE-3specific CD4$^+$ clones, in the continuous presence of preservative-free monoclonal antibodies used at a 1/20 dilution. Monoclonal antibody 2B6 (against HLA-DR) abolished the recognition whereas the recognition is unchanged in the presence of monoclonal antibody W6/32 (against HLA-A, B, C).

Example 2

Identification of the MAGE-3 HLA-DR Restricted Peptide

Figure 4:
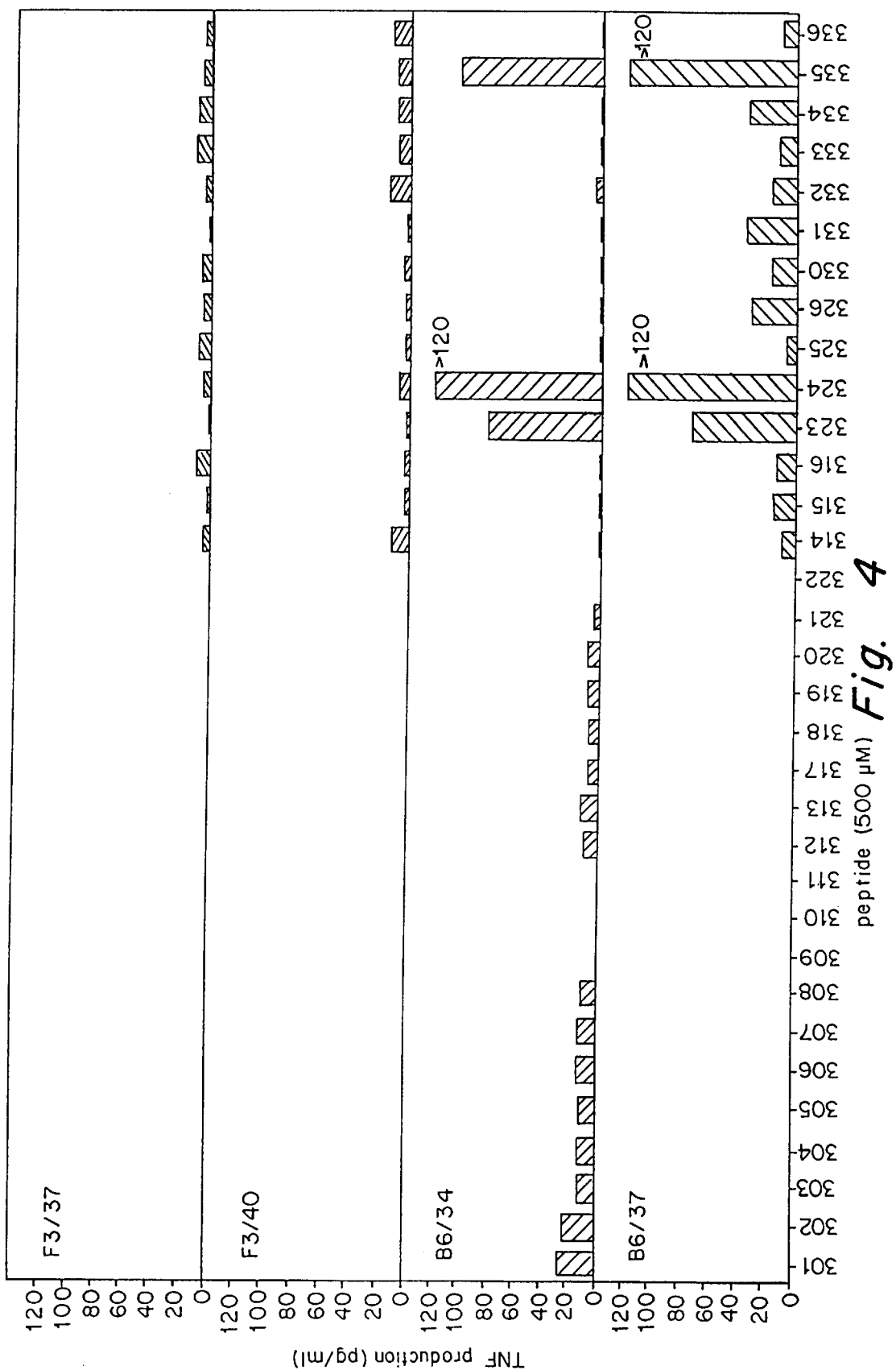
FIG. 4 is a graph detailing the screening of MAGE-3 peptides for recognition by CD4$^+$ clones B6/34, B6/37, F3/37 and F3/40.
Figure 5:
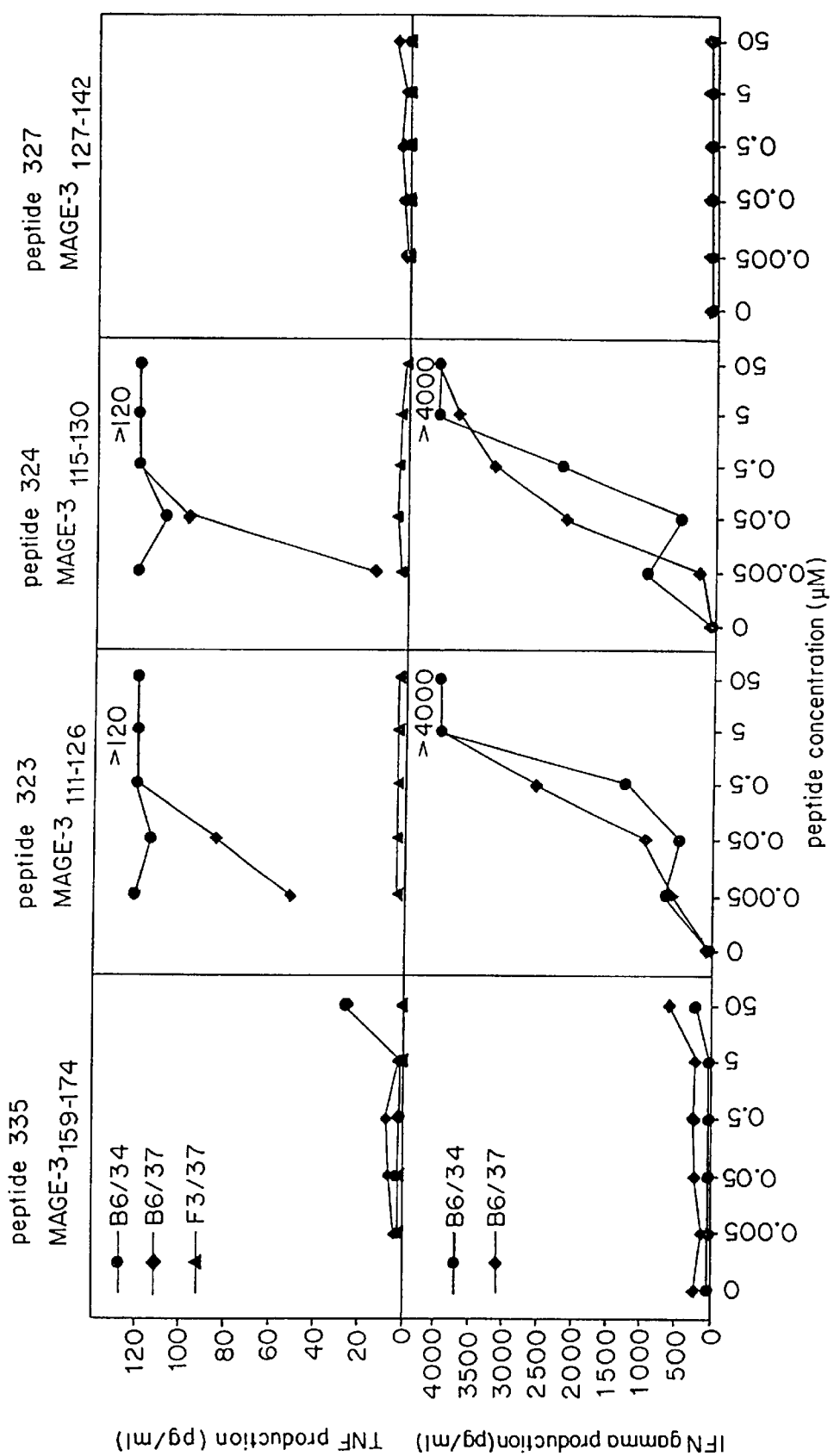
FIG. 5 is a graph depicting stimulation of TNF and IFN-$\gamma$ production by CD4$^+$ clones B6/34 and B6/37 EBV-B cells pulsed with the peptide RKVAELVHFLLLKYRA (MAGE-$3_{111\text{-}126}$, SEQ ID NO:3) or ELVHFLLLKYRAREPV (MAGE-$3_{115\text{-}130}$, SEQ ID NO:4).

In order to identify the MAGE-3 peptides recognized by these CD4 clones, 16 amino acid peptides, corresponding to parts of the MAGE-3 protein sequence were synthesized, loaded on the autologous EBV-B cells and tested for recognition (FIG. 4 and 5). Synthetic peptides were dissolved in DMSO (Merck) and used at a final concentration of 500 ktM or 50 µM. EBV-B cells (5,000 per round-bottomed microwell) were incubated 2 hours at 37° C., 8% $CO_2$ in the presence of the different peptides. CD4$^+$ clones were then added at 2,500 cells per well. Assay medium was Iscove's medium supplemented with L-glutamine, L-arginine, L-asparagine, 10% human serum and IL-2 (25 U/ml). After 18–20 hours, supernatants were harvested and assessed or TNF-α and IFN-γ secretion. IFN-γ production was measured using an ELISA test (20–4000 pg/ml) developed in the laboratory with reagents from Medgenix Diagnostics-Biosource (Fleurus, Belgium).

Figure 6:
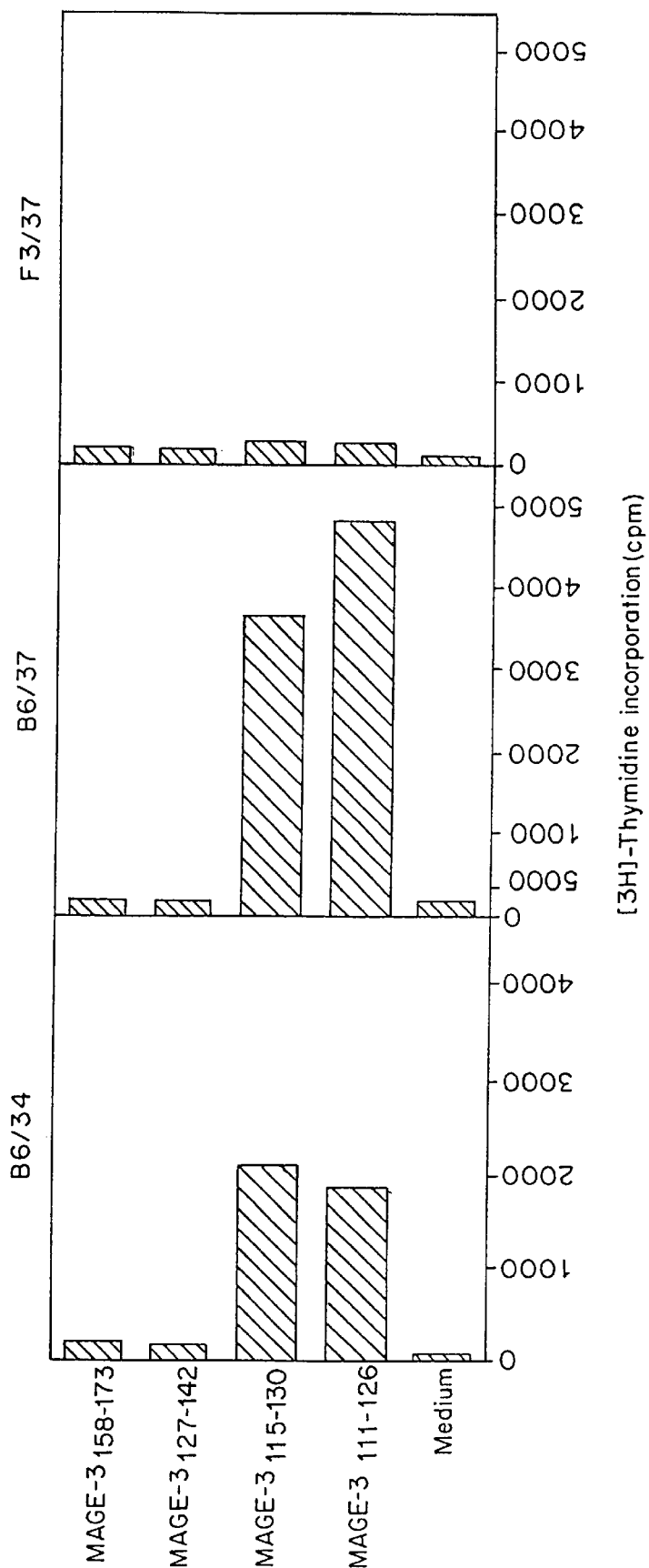
FIG. 6 is a graph which shows that autologous EBV-B cells pulsed with the peptide MAGE-$3_{111\text{-}126}$ or MAGE-$3_{115\text{-}130}$ induced the proliferation of clones B6/34 and B6/37.
Figure 7:
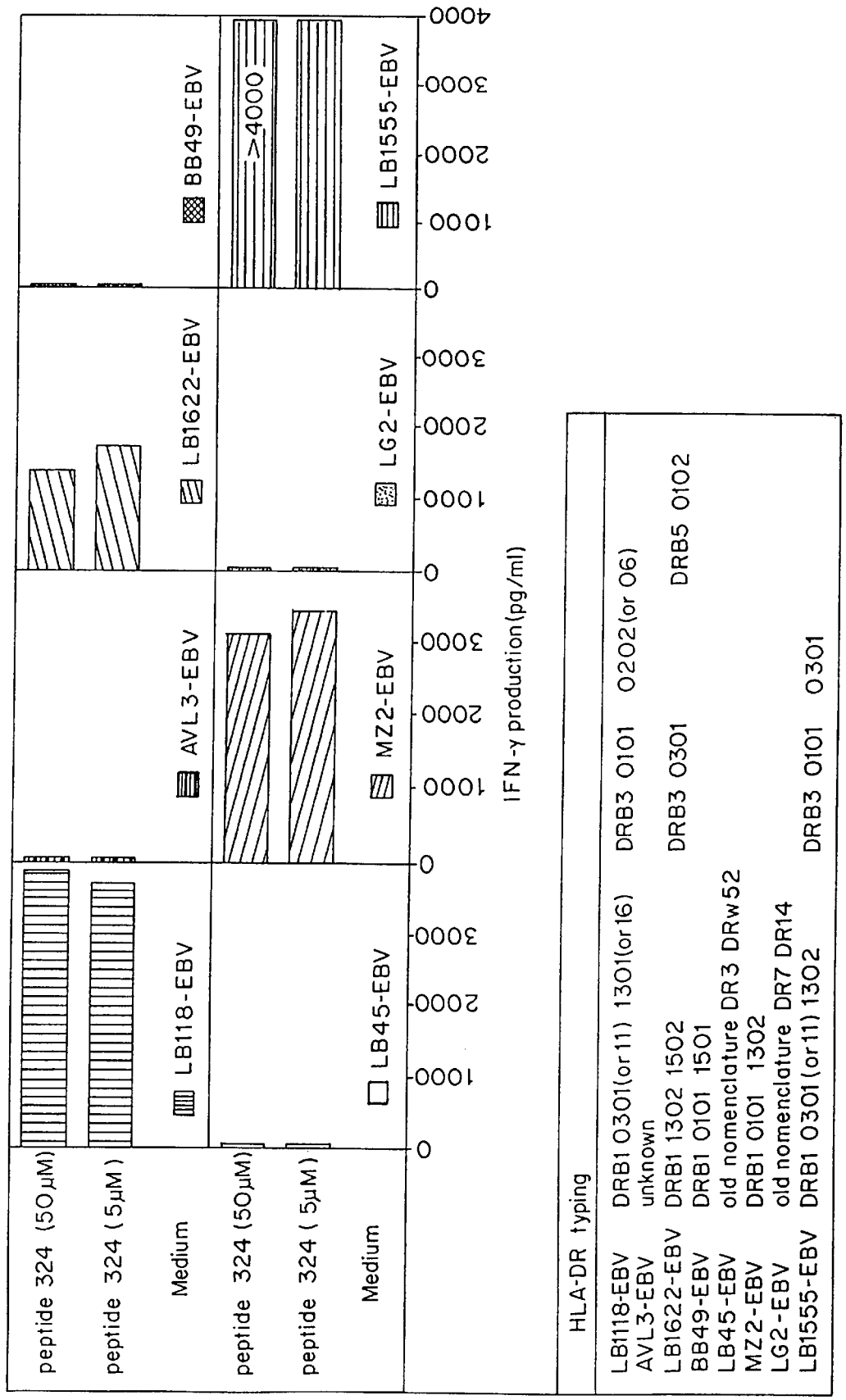
FIG. 7 is a graph which demonstrates that the response of CD4$^+$ clone B6/37 to peptide MAGE-$3_{115\text{-}130}$ is HLA-DRB1/1302 restricted.

In one set of experiments, the peptides were screened at a non-physiologic concentration of 500 µM. Non-physiologic concentrations of peptide may lead to non-specific activation of T cells clones. Indeed, when used at 500 µM, peptide MAGE-$3_{159-174}$ (FIG. 4-peptide 335; SEQ ID NO:6) induced activation of clones B6/34 and B6/37, but this peptide was not effective in activating these clones when used at 50 µM (FIG. 5). On the contrary, the peptides RKVAELVHFLLLKYRA (MAGE-$3_{111-126}$-FIG. 4-peptide 323; SEQ ID NO:3) and ELVHFLLLKYRAREPV (MAGE-$3_{115-130}$-FIG. 4-peptide 324; SEQ ID NO:4) stimulated specifically TNF-α and IFN-γ production by clones B6/34 and B6/37 when used at physiologic concentrations. These two peptides were also able to induce the proliferation of the B6 clones (FIG. 6).

Example 3

Determination of the HLA Restriction Element Utilized by MAGE-3 Specific CD4$^+$ Clone B6/34

Cytokine secretion by these CD4$^+$ clones in response to autologous EBV-B cell pulsed with the His-MAGE-3 protein is restricted to HLA-DR. To further define the HLA-restriction element utilized by clone B6/37, additional EBV-B cell lines were used for peptide presentation. HLA serotyping of AUMA-EBV, LB 1555-EBV, GERL-EBV revealed that class II molecules shared by all three cell types were limited to HLA-DRB1/1302. Moreover, ADET-EBV was found to present effectively the MAGE-$3_{115-130}$ peptide and the HLA serotyping of these cells was found to be HLA-DRB1/1301. Screening of several other EBV-B cell lines as described above for their ability to stimulate clones B6/34 and B6/37 when pulsed with peptide MAGE-$3_{115-130}$ is performed in order to confirm that both HLA-DRB 1/1301 and HLA-DRB 1/1302 can present the peptide, or to define other HLA-DRB1/13 presenting molecules.

Example 4

Determination of the Minimal Peptide Still Able to Stimulate B6/37 Clone

Figure 8:
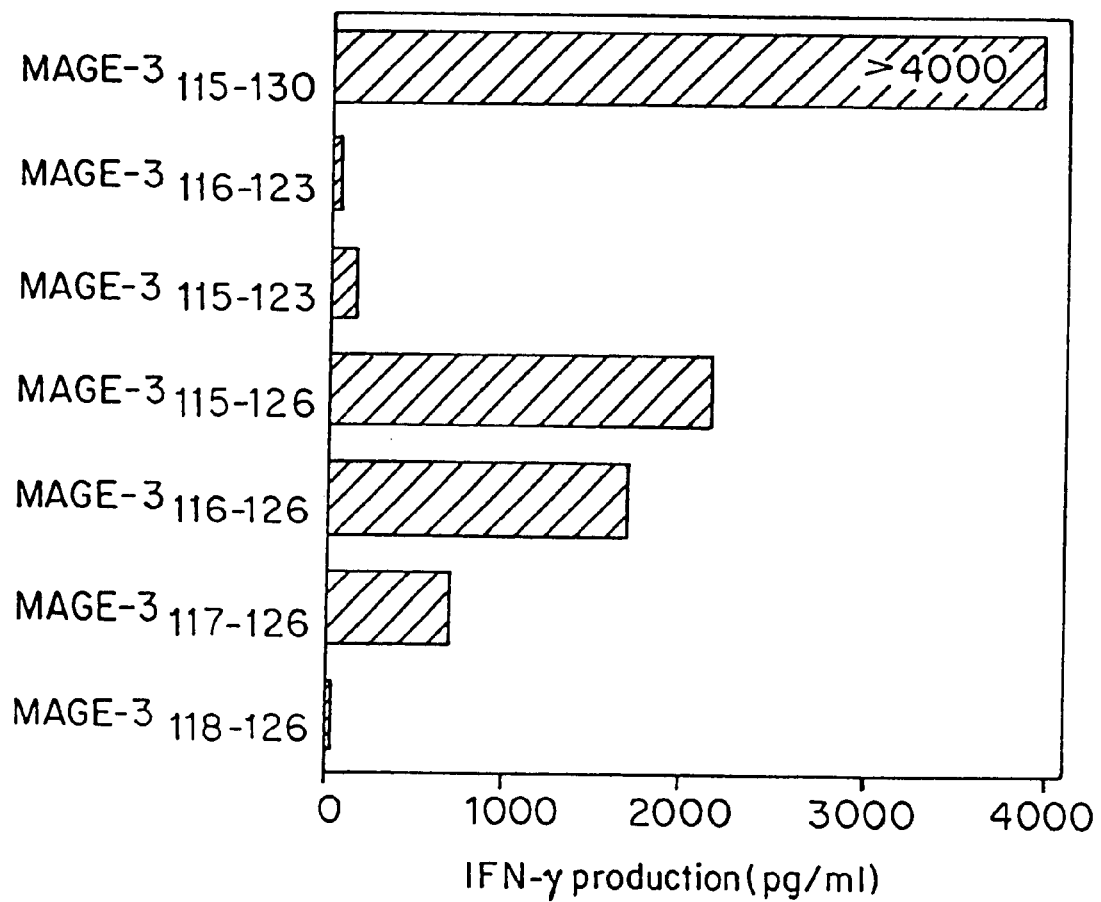
FIG. 8 is a graph which shows the reactivity of clone B6/37 against autologous EBV-B cells pulsed with truncated peptides derived from MAGE-$3_{115\text{-}130}$.

Unlike HLA-class I-restricted peptides, class II-restricted peptides vary considerably in length and can tolerate extensions at both the amino and carboxy termini. We demonstrated that both peptides MAGE-$3_{111-126}$ and MAGE-$3_{115-130}$ stimulated specifically clones B6/34 and B6/37, whereas peptides MAGE-$3_{107-122}$ and MAGE-$3_{119-134}$ were unable to activate these clones. Therefore, the MAGE-$3_{115-126}$ peptide (ELVHFLLLKYRA; SEQ ID NO:9) may be the minimal 12 amino-acids motif necessary for activation of B6/34 and B6/37 clones. As expected, peptide AGE-$3_{115-126}$ induced significant production of IFN-γ by clone B6/37 (FIG. 8). Shortened peptides having deletions of one residue or more also were prepared. Several of the shortened peptides, e.g. MAGE-$3_{116-126}$ (SEQ ID NO:10) and MAGE-$3_{117-126}$ (SEQ ID NO:11), also induced IFN-γ production by clone B6/37 (FIG. 8), albeit reduced amounts of IFN-γ. MAGE-$3_{118-126}$ (SEQ ID NO:12) did not induce the production of significant amounts of IFN-γ.

Other aspects of the invention will be clear to the skilled artisan and need not be repeated here. Each reference cited herein is incorporated by reference in its entirety.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. An isolated nucleic acid encoding a HLA class II binding peptide, wherein the peptide comprises a fragment of MAGE-3 polypeptide, which fragment consists of an amino acid sequence selected from the group consisting of SEQ ID NO:11, and SEQ ID NO:11 having 1–10 amino acids added to either or both ends.

2. The isolated nucleic acid of claim 1, wherein the fragment of MAGE-3 polypeptide is encoded by a nucleic acid comprising SEQ ID NO:13.

3. An expression vector comprising the isolated nucleic acid of claim 1 operably linked to a promoter.

4. The expression vector of claim 3 wherein the fragment of MAGE-3 polypeptide is encoded by a nucleic acid comprising SEQ ID NO:13.

5. The expression vector of claim 4 further comprising a nucleic acid which encodes an HLA-DRB1/13 molecule.

6. A host cell transfected or transformed with the expression vector of claim 4.

7. A host cell transfected or transformed with the expression vector of claim 4, and wherein the host cell expresses an HLA-DRB1/13 molecule.

8. The expression vector of claim 3 further comprising a nucleic acid which encodes an HLA-DRB1/13 molecule.

9. A host cell transfected or transformed with the expression vector of claim 8.

10. A host cell transfected or transformed with the expression vector claim 3.

11. A host cell transfected or transformed with the expression vector of claim 3, and wherein the host cell expresses an HLA-DRB1/13 molecule.

12. The expression vector of claim 3, wherein the HLA class II binding peptide is expressed as a fusion protein which contains an endosomal targeting signal.

13. The isolated nucleic acid of claim 1 wherein the fragment of MAGE-3 polypeptide comprises the amino acid sequence of SEQ ID NO:9.

14. The isolated nucleic acid of claim 1 wherein the fragment of MAGE-3 polypeptide comprises an amino acid sequence selected from the group consisting of SEQ ID NO:3, SEQ ID NO:4 and SEQ ID NO:10.

15. The isolated nucleic acid of claim 1 wherein the peptide consists of an amino acid sequence selected from the group consisting of SEQ ID NO:3 and SEQ ID NO:4.

16. An isolated nucleic acid molecule encoding a peptide which specifically binds to HLA class II molecules and which inhibits the stimulation of a T cell by a complex of a peptide comprising the amino acid sequence of SEQ ID NO:11 and a HLA class II molecule.

17. An isolated nucleic acid molecule encoding a peptide which specifically binds to HLA class II molecules and which inhibits the binding to a HLA class II molecule of a peptide comprising the amino acid sequence of SEQ ID NO:11.

* * * * *

SEQUENCE LISTING

<160> NUMBER OF SEQ ID NOS: 13

<210> SEQ ID NO 1
<211> LENGTH: 4204

-continued

```
<212> TYPE: DNA
<213> ORGANISM: Homo sapiens
<220> FEATURE:
<221> NAME/KEY: CDS
<222> LOCATION: 2465..3406

<400> SEQUENCE: 1
acgcaggcag tgatgtcacc cagaccacac cccttccccc aatgccactt caggggtac      60 tcagagtcag agacttggtc tgaggggagc agaagcaatc tgcagaggat ggcggtccag     120
gctcagccag gcatcaactt caggaccctg agggatgacc gaaggccccg cccacccacc     180
cccaactccc ccgaccccac caggatctac agcctcagga cccccgtccc aatccttacc     240
ccttgcccca tcaccatctt catgcttacc tccaccccca tccgatcccc atccaggcag     300
aatccagttc caccccctgcc cggaacccag gtagtaccg ttgccaggat gtgacgccac     360
tgacttgcgc attggaggtc agaagaccgc gagattctcg ccctgagcaa cgagcgacgg     420
cctgacgtcg gcggagggaa gccggcccag gctcggtgag gaggcaaggt aagacgctga     480
gggaggactg aggcgggcct cacctcagac agagggcctc aaataatcca gtgctgcctc     540
tgctgccggg cctgggccac cccgcagggg aagacttcca ggctgggtcg ccactacctc     600
accccgccga ccccgccgc tttagccacg gggaactctg gggacagagc ttaatgtggc     660
cagggcaggg ctggttagaa gaggtcaggg cccacgctgt ggcaggaatc aaggtcagga     720
ccccgagagg gaactgaggg cagcctaacc accaccctca ccaccattcc cgtcccccaa     780
cacccaaccc caccccccatc ccccattccc atccccaccc caccctat cctggcagaa     840 tccgggcttt gccctggta tcaagtcacg gaagctccgg gaatggcggc caggcacgtg     900
agtcctgagg ttcacatcta cggctaaggg agggaagggg ttcggtatcg cgagtatggc     960
cgttgggagg cagcgaaagg gcccaggcct cctggaagac agtggagtcc tgagggacc    1020 cagcatgcca ggacaggggg cccactgtac ccctgtctca aaccgaggca ccttttcatt    1080
cggctacggg aatcctaggg atgcagaccc acttcagcag ggggttgggg cccagccctg    1140
cgaggagtca tggggaggaa gaagaggag gactgagggg accttggagt ccagatcagt    1200
ggcaaccttg ggctggggga tgctgggcac agtggccaaa tgtgctctgt gctcattgcg    1260
ccttcagggt gaccagagag ttgagggctg tggtctgaag agtgggactt caggtcagca    1320
gagggaggaa tcccaggatc tgcagggccc aaggtgtacc cccaagggc ccctatgtgg    1380 tggacagatg cagtggtcct aggatctgcc aagcatccag gtgaagagac tgagggagga    1440
ttgagggtac ccctgggaca gaatgcggac tgggggcccc ataaaaatct gccctgctcc    1500
tgctgttacc tcagagagcc tgggcagggc tgtcagctga ggtccctcca ttatcctagg    1560
atcactgatg tcagggaagg ggaagccttg gtctgagggg gctgcactca gggcagtaga    1620
gggaggctct cagaccctac taggagtgga ggtgaggacc aagcagtctc ctacccagg    1680 gtacatggac ttcaataaat ttggacatct ctcgttgtcc tttccgggag gacctgggaa    1740
tgtatggcca gatgtgggtc ccctcatgtt tttctgtacc atatcaggta tgtgagttct    1800
tgacatgaga gattctcagg ccagcagaag ggagggatta ggccctataa ggagaaaggt    1860
gagggccctg agtgagcaca gagggatcc tccaccccag tagagtgggg acctcacaga    1920
gtctggccaa ccctcctgac agttctggga atccgtggct gcgtttgctg tctgcacatt    1980
ggggccccgt ggattcctct cccaggaatc aggagctcca ggaacaaggc agtgaggact    2040
tggtctgagg cagtgtcctc aggtcacaga gtagaggggg ctcagatagt gccaacggtg    2100
aaggtttgcc ttggattcaa accaagggcc ccacctgccc cagaacacat ggactccaga    2160
```

-continued

```
gcgcctggcc tcaccctcaa tactttcagt cctgcagcct cagcatgcgc tggccggatg    2220
taccctgagg tgccctctca cttcctcctt caggttctga ggggacaggc tgacctggag    2280
gaccagaggc ccccggagga gcactgaagg agaagatctg taagtaagcc tttgttagag    2340
cctccaaggt tccattcagt actcagctga ggtctctcac atgctccctc tctcccagg    2400 ccagtgggtc tccattgccc agctcctgcc cacactcccg cctgttgccc tgaccagagt    2460 catc atg cct ctt gag cag agg agt cag cac tgc aag cct gaa gaa ggc    2509
     Met Pro Leu Glu Gln Arg Ser Gln His Cys Lys Pro Glu Glu Gly
      1               5                  10                  15 ctt gag gcc cga gga gag gcc ctg ggc ctg gtg ggt gcg cag gct cct    2557
Leu Glu Ala Arg Gly Glu Ala Leu Gly Leu Val Gly Ala Gln Ala Pro
                 20                  25                  30 gct act gag gag cag gag gct gcc tcc tcc tct tct act cta gtt gaa    2605
Ala Thr Glu Glu Gln Glu Ala Ala Ser Ser Ser Ser Thr Leu Val Glu
             35                  40                  45 gtc acc ctg ggg gag gtg cct gct gcc gag tca cca gat cct ccc cag    2653
Val Thr Leu Gly Glu Val Pro Ala Ala Glu Ser Pro Asp Pro Pro Gln
 50                  55                  60 agt cct cag gga gcc tcc agc ctc ccc act acc atg aac tac cct ctc    2701
Ser Pro Gln Gly Ala Ser Ser Leu Pro Thr Thr Met Asn Tyr Pro Leu
     65                  70                  75 tgg agc caa tcc tat gag gac tcc agc aac caa gaa gag gag ggg cca    2749
Trp Ser Gln Ser Tyr Glu Asp Ser Ser Asn Gln Glu Glu Glu Gly Pro
 80                  85                  90                  95 agc acc ttc cct gac ctg gag tcc gag ttc caa gca gca ctc agt agg    2797
Ser Thr Phe Pro Asp Leu Glu Ser Glu Phe Gln Ala Ala Leu Ser Arg
                 100                 105                 110 aag gtg gcc gag ttg gtt cat ttc ctg ctc ctc aag tat cga gcc agg    2845
Lys Val Ala Glu Leu Val His Phe Leu Leu Leu Lys Tyr Arg Ala Arg
             115                 120                 125 gag ccg gtc aca aag gca gaa atg ctg ggg agt gtc gtc gga aat tgg    2893
Glu Pro Val Thr Lys Ala Glu Met Leu Gly Ser Val Val Gly Asn Trp
         130                 135                 140 cag tat ttc ttt cct gtg atc ttc agc aaa gct tcc agt tcc ttg cag    2941
Gln Tyr Phe Phe Pro Val Ile Phe Ser Lys Ala Ser Ser Ser Leu Gln
     145                 150                 155 ctg gtc ttt ggc atc gag ctg atg gaa gtg gac ccc atc ggc cac ttg    2989
Leu Val Phe Gly Ile Glu Leu Met Glu Val Asp Pro Ile Gly His Leu
160                 165                 170                 175 tac atc ttt gcc acc tgc ctg ggc ctc tcc tac gat ggc ctg ctg ggt    3037
Tyr Ile Phe Ala Thr Cys Leu Gly Leu Ser Tyr Asp Gly Leu Leu Gly
                 180                 185                 190 gac aat cag atc atg ccc aag gca ggc ctc ctg ata atc gtc ctg gcc    3085
Asp Asn Gln Ile Met Pro Lys Ala Gly Leu Leu Ile Ile Val Leu Ala
             195                 200                 205 ata atc gca aga gag ggc gac tgt gcc cct gag gag aaa atc tgg gag    3133
Ile Ile Ala Arg Glu Gly Asp Cys Ala Pro Glu Glu Lys Ile Trp Glu
         210                 215                 220 gag ctg agt gtg tta gag gtg ttt gag ggg agg gaa gac agt atc ttg    3181
Glu Leu Ser Val Leu Glu Val Phe Glu Gly Arg Glu Asp Ser Ile Leu
     225                 230                 235 ggg gat ccc aag aag ctg ctc acc caa cat ttc gtg cag gaa aac tac    3229
Gly Asp Pro Lys Lys Leu Leu Thr Gln His Phe Val Gln Glu Asn Tyr
240                 245                 250                 255 ctg gag tac cgg cag gtc ccc ggc agt gat cct gca tgt tat gaa ttc    3277
Leu Glu Tyr Arg Gln Val Pro Gly Ser Asp Pro Ala Cys Tyr Glu Phe
                 260                 265                 270 ctg tgg ggt cca agg gcc ctc gtt gaa acc agc tat gtg aaa gtc ctg    3325
```

```
                                                                 -continued

Leu Trp Gly Pro Arg Ala Leu Val Glu Thr Ser Tyr Val Lys Val Leu
            275                 280                 285 cac cat atg gta aag atc agt gga gga cct cac att tcc tac cca ccc      3373
His His Met Val Lys Ile Ser Gly Gly Pro His Ile Ser Tyr Pro Pro
            290                 295                 300 ctg cat gag tgg gtt ttg aga gag ggg gaa gag tgagtctgag cacgagttgc    3426
Leu His Glu Trp Val Leu Arg Glu Gly Glu Glu
            305                 310 agccagggcc agtgggaggg ggtctgggcc agtgcacctt ccggggccgc atcccttagt    3486
ttccactgcc tcctgtgacg tgaggcccat tcttcactct ttgaagcgag cagtcagcat    3546
tcttagtagt gggtttctgt tctgttggat gactttgaga ttattctttg tttcctgttg    3606
gagttgttca aatgttcctt ttaacggatg gttgaatgag cgtcagcatc caggtttatg    3666
aatgacagta gtcacacata gtgctgttta tatagtttag gagtaagagt cttgtttttt    3726
actcaaattg ggaaatccat tccattttgt gaattgtgac ataataatag cagtggtaaa    3786
agtatttgct taaaattgtg agcgaattag caataacata catgagataa ctcaagaaat    3846
caaaagatag ttgattcttg ccttgtacct caatctattc tgtaaaatta acaaatatg     3906
caaaccagga tttccttgac ttctttgaga atgcaagcga aattaaatct gaataaataa    3966
ttcttcctct tcactggctc gtttcttttc cgttcactca gcatctgctc tgtgggaggc    4026
cctgggttag tagtggggat gctaaggtaa gccagactca cgcctaccca tagggctgta    4086
gagcctagga cctgcagtca tataattaag gtggtgagaa gtcctgtaag atgtagagga    4146
aatgtaagag agggtgagg gtgtggcgct ccgggtgaga gtagtggagt gtcagtgc      4204

<210> SEQ ID NO 2
<211> LENGTH: 314
<212> TYPE: PRT
<213> ORGANISM: Homo sapiens

<400> SEQUENCE: 2

Met Pro Leu Glu Gln Arg Ser Gln His Cys Lys Pro Glu Glu Gly Leu
 1               5                  10                  15

Glu Ala Arg Gly Glu Ala Leu Gly Leu Val Gly Ala Gln Ala Pro Ala
            20                  25                  30

Thr Glu Gln Glu Ala Ala Ser Ser Ser Thr Leu Val Glu Val
            35                  40                  45

Thr Leu Gly Glu Val Pro Ala Ala Glu Ser Pro Asp Pro Gln Ser
 50                  55                  60

Pro Gln Gly Ala Ser Ser Leu Pro Thr Thr Met Asn Tyr Pro Leu Trp
 65                  70                  75                  80

Ser Gln Ser Tyr Glu Asp Ser Ser Asn Gln Glu Glu Glu Gly Pro Ser
            85                  90                  95

Thr Phe Pro Asp Leu Glu Ser Glu Phe Gln Ala Ala Leu Ser Arg Lys
            100                 105                 110

Val Ala Glu Leu Val His Phe Leu Leu Leu Lys Tyr Arg Ala Arg Glu
            115                 120                 125

Pro Val Thr Lys Ala Glu Met Leu Gly Ser Val Val Gly Asn Trp Gln
            130                 135                 140

Tyr Phe Phe Pro Val Ile Phe Ser Lys Ala Ser Ser Ser Leu Gln Leu
145                 150                 155                 160

Val Phe Gly Ile Glu Leu Met Glu Val Asp Pro Ile Gly His Leu Tyr
            165                 170                 175

Ile Phe Ala Thr Cys Leu Gly Leu Ser Tyr Asp Gly Leu Leu Gly Asp
```

```
                  180                 185                 190
Asn Gln Ile Met Pro Lys Ala Gly Leu Leu Ile Ile Val Leu Ala Ile
                195                 200                 205
Ile Ala Arg Glu Gly Asp Cys Ala Pro Glu Lys Ile Trp Glu Glu
    210                 215                 220
Leu Ser Val Leu Glu Val Phe Glu Gly Arg Glu Asp Ser Ile Leu Gly
225                 230                 235                 240
Asp Pro Lys Lys Leu Leu Thr Gln His Phe Val Gln Glu Asn Tyr Leu
                245                 250                 255
Glu Tyr Arg Gln Val Pro Gly Ser Asp Pro Ala Cys Tyr Glu Phe Leu
                260                 265                 270
Trp Gly Pro Arg Ala Leu Val Glu Thr Ser Tyr Val Lys Val Leu His
                275                 280                 285
His Met Val Lys Ile Ser Gly Gly Pro His Ile Ser Tyr Pro Pro Leu
                290                 295                 300
His Glu Trp Val Leu Arg Glu Gly Glu Glu
305                 310

<210> SEQ ID NO 3
<211> LENGTH: 16
<212> TYPE: PRT
<213> ORGANISM: Homo sapiens

<400> SEQUENCE: 3

Arg Lys Val Ala Glu Leu Val His Phe Leu Leu Leu Lys Tyr Arg Ala
1               5                  10                  15

<210> SEQ ID NO 4
<211> LENGTH: 16
<212> TYPE: PRT
<213> ORGANISM: Homo sapiens

<400> SEQUENCE: 4

Glu Leu Val His Phe Leu Leu Leu Lys Tyr Arg Ala Arg Glu Pro Val
1               5                  10                  15

<210> SEQ ID NO 5
<211> LENGTH: 16
<212> TYPE: PRT
<213> ORGANISM: Homo sapiens

<400> SEQUENCE: 5

Arg Glu Pro Val Thr Lys Ala Glu Met Leu Gly Ser Val Val Gly Asn
1               5                  10                  15

<210> SEQ ID NO 6
<211> LENGTH: 16
<212> TYPE: PRT
<213> ORGANISM: Homo sapiens

<400> SEQUENCE: 6

Gln Leu Val Phe Gly Ile Glu Leu Met Glu Val Asp Pro Ile Gly His
1               5                  10                  15

<210> SEQ ID NO 7
<211> LENGTH: 8
<212> TYPE: PRT
<213> ORGANISM: Homo sapiens

<400> SEQUENCE: 7

Leu Val His Phe Leu Leu Leu Lys
```

-continued

```
<210> SEQ ID NO 8
<211> LENGTH: 9
<212> TYPE: PRT
<213> ORGANISM: Homo sapiens

<400> SEQUENCE: 8

Glu Leu Val His Phe Leu Leu Leu Lys
 1               5

<210> SEQ ID NO 9
<211> LENGTH: 12
<212> TYPE: PRT
<213> ORGANISM: Homo sapiens

<400> SEQUENCE: 9

Glu Leu Val His Phe Leu Leu Leu Lys Tyr Arg Ala
 1               5                  10

<210> SEQ ID NO 10
<211> LENGTH: 11
<212> TYPE: PRT
<213> ORGANISM: Homo sapiens

<400> SEQUENCE: 10

Leu Val His Phe Leu Leu Leu Lys Tyr Arg Ala
 1               5                  10

<210> SEQ ID NO 11
<211> LENGTH: 10
<212> TYPE: PRT
<213> ORGANISM: Homo sapiens

<400> SEQUENCE: 11

Val His Phe Leu Leu Leu Lys Tyr Arg Ala
 1               5                  10

<210> SEQ ID NO 12
<211> LENGTH: 9
<212> TYPE: PRT
<213> ORGANISM: Homo sapiens

<400> SEQUENCE: 12

His Phe Leu Leu Leu Lys Tyr Arg Ala
 1               5

<210> SEQ ID NO 13
<211> LENGTH: 30
<212> TYPE: DNA
<213> ORGANISM: Homo sapiens

<400> SEQUENCE: 13
gttcattttc tgctcctcaa gtatcgagcc                                    30
```